(12) United States Patent
Sur et al.

(10) Patent No.: US 11,468,327 B2
(45) Date of Patent: Oct. 11, 2022

(54) DIFFERENTIAL LEARNING FOR LEARNING NETWORKS

(71) Applicant: GE Precision Healthcare LLC, Milwaukee, WI (US)

(72) Inventors: Chiranjib Sur, San Ramon, CA (US); Venkata Ratnam Saripalli, Danville, CA (US); Gopal B. Avinash, San Ramon, CA (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 220 days.

(21) Appl. No.: 16/883,315

(22) Filed: May 26, 2020

(65) Prior Publication Data

US 2021/0374513 A1    Dec. 2, 2021

(51) Int. Cl.
*G06N 3/08* (2006.01)
*G16H 50/20* (2018.01)
*G16H 30/40* (2018.01)
*G06N 3/04* (2006.01)
*G06T 7/00* (2017.01)

(52) U.S. Cl.
CPC .............. *G06N 3/08* (2013.01); *G06N 3/04* (2013.01); *G06T 7/0012* (2013.01); *G16H 30/40* (2018.01); *G16H 50/20* (2018.01); *G06T 2207/20081* (2013.01); *G06T 2207/20084* (2013.01); *G06T 2207/30004* (2013.01)

(58) Field of Classification Search
CPC ........ G06N 20/00; G06N 3/0454; G06N 3/08; G06N 3/084; G06N 3/0445; G06N 3/006; G06N 3/04; G06N 3/063; G06N 3/0481; G06N 3/088; G06N 3/105; G06N 5/043; G06N 7/005; G06N 20/10
USPC .......................................................... 706/21
See application file for complete search history.

(56) References Cited

U.S. PATENT DOCUMENTS

2016/0335536 A1\* 11/2016 Yamazaki ................ G06N 3/08
2020/0302303 A1\* 9/2020 Chen ...................... G06N 3/084

\* cited by examiner

*Primary Examiner* — Ajibola A Akinyemi
(74) *Attorney, Agent, or Firm* — Amin, Turocy & Watson, LLP

(57) ABSTRACT

A computer-implemented system is provided that includes a learning network component that determines respective weights assigned to respective node inputs of the learning network in accordance with a learning phase of the learning network and trains a variable separator component to differentially change learning rates of the learning network component. A differential rate component applies at least one update learning rate to adjust at least one weight assigned to at least one of the respective node inputs and applies at least one other update learning rate to adjust the respective weight assigned to at least one other of the respective node inputs in accordance with the variable separator component during the learning phase of the learning network. A differential rate component applies at least one update rate to adjust at least one weight assigned to at least one of the respective node inputs and applies at least one other update rate to adjust the respective weight assigned to at least one other of the respective node inputs in accordance with the learning phase of the learning network.

20 Claims, 10 Drawing Sheets

DIFFERENTIAL LEARNING FOR LEARNING NETWORKS

TECHNICAL FIELD

The subject disclosure relates to artificial intelligence (AI) systems, and more specifically to a learning component that applies differential update rates for weights that are assigned to different node inputs (or node input subsets) during a learning phase of the AI system to substantially mitigate processor learning time of the learning phase and also, improve predictive performance of the AI system subsequent to training.

BACKGROUND

Trained artificial intelligence (AI) systems process node inputs that enable predictions based on classes or features that have been previously categorized during a training/learning phase of the system. The AI systems can be trained to identify instances related to classes or features and thus, generate output predictions based on a given state of input variables supplied to different nodes of the network and processed at a given time. For instance, such systems can be trained to classify facial features and thus, identify a given person based on such classification (e.g., identify a given person based on nose feature, hairline feature, eye size feature, and eye spacing feature, and so forth). Before suitably accurate output predictions can be generated by AI systems however, inputs to the system and intermediate node inputs of the system representing different combinations of the respective inputs are weighted during a training/learning phase of the system.

Training enables predictive portion of the AI system to recognize the importance of each respective input supplied thereto for generating future predictions. This recognition for a given class can be determined during the training phase of the AI system, where system inputs and subsequent inner-layer input combinations receive training data to evaluate prediction accuracy. System inputs and input combinations are algorithmically weighted in the training phase, where each system variable is assigned a weighted value indicating its respective importance to the output prediction. As part of the training/learning process, output of the AI system is fed back after comparing with expected prediction based on training data that evaluates the accuracy associated with a given set of assigned weights. This evaluation of the learning network (weights of the network) continues as an algorithmic "trial and error" process until a desired level of prediction accuracy has been achieved. As is common experience among computer scientists and engineers, the algorithmic performance determination/evaluation of learning network during the training phase of an AI system can be an enormously complex and time-intensive processor task that increases exponentially as the number of system inputs for a training batch increases.

SUMMARY

The following presents a summary to provide a basic understanding of one or more examples of the invention. This summary is not intended to identify key or critical elements or delineate any scope of the different examples or any scope of the claims. Its sole purpose is to present concepts in a simplified form as a prelude to the more detailed description that is presented later. In one or more examples, systems, computer-implemented methods, apparatus and/or computer program products are described herein that facilitate imaging diagnostics in one example.

According to an example, a system, comprises a memory that stores computer-executable components; and a processor, operably coupled to the memory, that executes the computer-executable components stored in the memory. The computer-executable components comprise: a learning network component that determines respective weights assigned to respective node inputs of a learning network in accordance with a learning phase of the learning network and trains a variable separator component to differentially change learning rates of the learning network component; and a differential rate component that applies at least one update learning rate to adjust at least one weight assigned to at least one of the respective node inputs and applies at least one other update learning rate to adjust the respective weight assigned to at least one other of the respective node inputs in accordance with the variable separator component during the learning phase of the learning network.

In another example, A computer-implemented method, comprises: determining, by a system operatively coupled to a processor, respective weights assigned to respective node inputs of a learning network in accordance with a learning phase of the learning network; applying, by the system, at least one update rate to adjust at least one weight assigned to at least one of the respective node inputs; and applying, by the system, at least one other update rate to adjust the respective weight assigned to at least one other of the respective node inputs in accordance with the learning phase of the learning network.

In another example, a non-transitory machine-readable storage medium comprising executable instructions that, when executed by a processor cause the processor to determine respective weights assigned to respective node inputs of a learning network in accordance with a learning phase of the learning network. The instructions cause the processor to apply at least one update rate to adjust at least one weight assigned to at least one of the respective node inputs. The instructions cause the processor to apply at least one other update rate to adjust the respective weight assigned to at least one other of the respective node inputs in accordance with the learning phase of the learning network.

In some examples, elements described in connection with the disclosed systems can be embodied in different forms such as a computer-implemented method, a computer program product, or another form.

DETAILED DESCRIPTION

Figure 1:
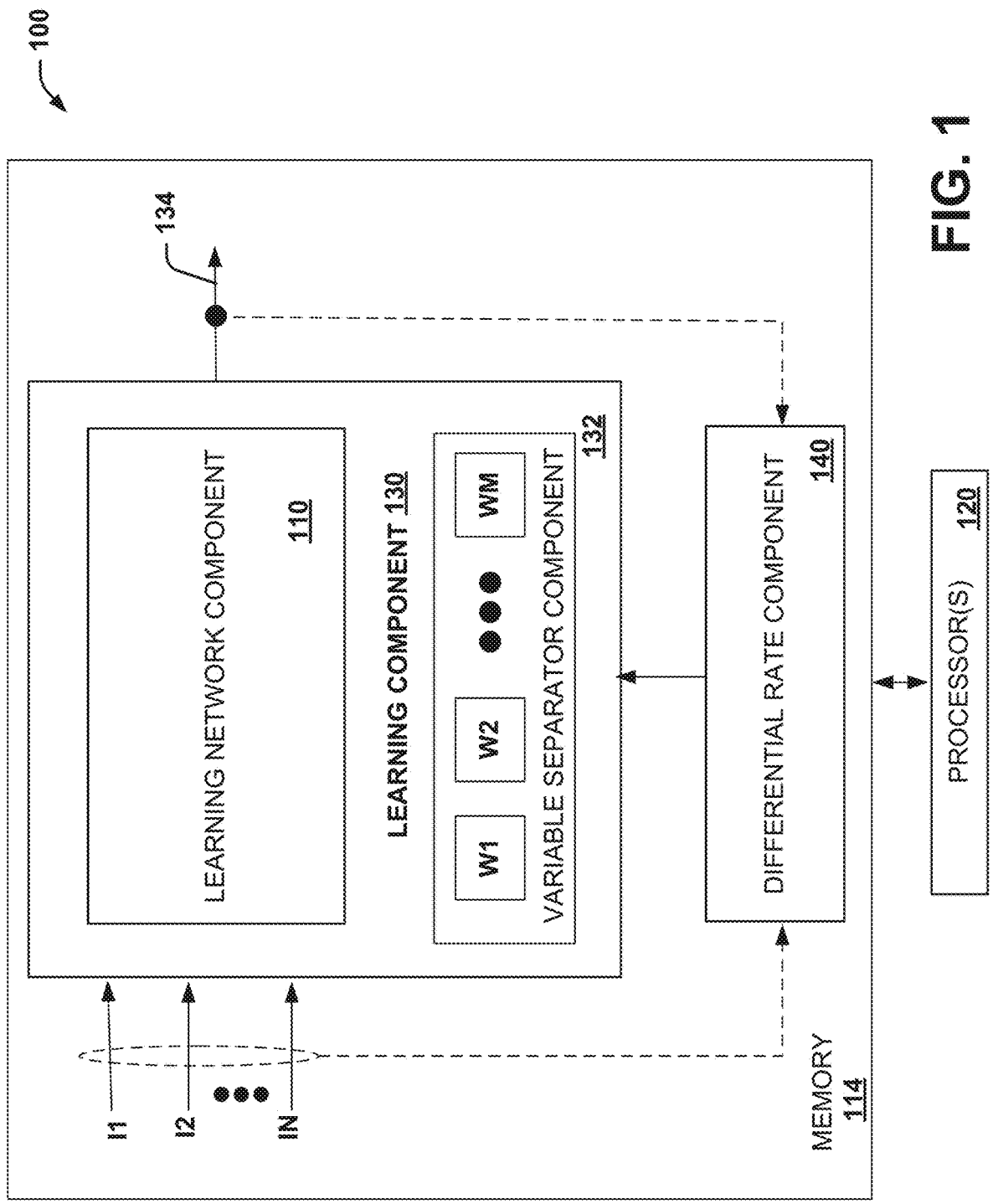
FIG. 1 illustrates a block diagram of an example system that employs differential update rates to facilitate learning and performance of a learning network, in accordance with one or more examples of the disclosed subject matter.

The following detailed description is merely illustrative and is not intended to limit examples illustrated and described herein and/or application or uses of such examples. Furthermore, there is no intention to be bound by any expressed or implied information presented in the preceding Summary section or in the Detailed Description section.

The disclosed subject matter is directed to a learning component that applies differential update rates for weights that are assigned to different training inputs (or input subsets) during a learning phase of the AI system to substantially mitigate processor learning time of the learning phase and also, improve predictive performance of the AI system subsequent to training. Before discussion of such improvements, conventional AI system (e.g., neural network system) training begins with an initial assignment of weights to inputs that are associated with nodes of the system. Training data is then supplied to AI system node inputs (including input nodes and intermediate nodes of the network). Based on the assigned weights for the respective node inputs and which ripple as different combinations of the respective node inputs throughout the network, where system prediction output is evaluated algorithmically to observe accuracy (e.g., via statistical error loss functions) based on the assigned weights for a given batch and in view of known qualities of the training data.

Weights are conventionally adjusted incrementally and uniformly across the input node set and throughout the network, where the value of weight adjustment per round of evaluation is referred to as the update rate. Subsequent prediction evaluations are executed in accordance with network learning until a desired level of prediction accuracy has been achieved. The final assignment of weights to respective system node inputs in accordance with the learning/training phase of the AI system, and that also yields suitable prediction accuracy, are subsequently employed going forward to generate future predictions in a "trained network." The respective trained network can then classify/process data that has not been previously evaluated in training wherein the learning/evaluation components described herein are disabled.

Conventional evaluation of weights (learning network) are known to be a massively intensive and time-consuming processor task during training. To train the number of nodes combinations in even a modest network of nodes leads to the problem that to attempt to train all the respective combinations—even with the fastest and most sophisticated processors, would take more training time than reasonable humans are willing to wait for the respective combinations to be exhaustively evaluated in such a manner. Thus, to achieve reasonable training times with respect to determining weights in the network, statistical evaluation algorithms have been developed that allow evaluation of a suitable amount of such combinations in a reasonable amount of time, while also yielding reasonable prediction accuracy from the network subsequent to training. For example, a simple, three input node learning network, having four intermediate nodes to account for the different combinations of node inputs and one output node can involve large numbers of weights updates to be evaluated/adjusted in accordance with training/learning.

Evaluation often involves setting weights for the network, supplying training data to the network, and evaluating the prediction of output of the network according to error calculations metrics. Such network evaluation can involve what is known as backpropagation where error optimization algorithms such as gradient descent are performed for better training of the network in an attempt to reduce the amount of computational prediction error involved in evaluation of the network for a prediction accuracy. Traditional learning systems employ the strategy of setting uniform update rates (e.g., each weight statistically adjusted by the same learning rate value per iteration for a batch of training data). Thus, for substantially all node inputs, weights are adjusted for respective node inputs of the network using uniform update rates during the respective rounds the learning phase. This uniform update rate weighting strategy unfortunately can significantly increase learning time and thus can reduce prediction accuracy after training since prediction accuracy is limited, by definition, by the statistical error evaluation processes described herein. Thus, significant processing time is expended for evaluation that often causes foregoing further weight adjustment which therefore can reduce further improvement of prediction accuracy. The differential rate weight adjustment processes described herein can overcome these and other deficiencies of setting/evaluating weights as described herein.

The differential rate determinations described herein allows learning components to focus on and prioritize desired problem areas (e.g., designated regions of an image). Thus, in one example, a given update rate can be employed for the learning problem area of interest while one or more other update rates can be employed for other areas of the network. For instance, a subset of update rates can be provided for parts of the overall classification problem that are not deemed as important to a given problem task at hand. For example, an image may be analyzed having a given feature/region of the image deemed more relevant for further analytical weighting based on a relevance criterion whereas other parts of the image may not be deemed as such. By applying different update rates for weight adjustment to prioritize areas/problems of interest and thus, utilizing other update rates for other parts of the network, learning time can be significantly reduced. Moreover, employing differential learning also can increase future prediction accuracy of the network for identified areas of interest that can be trained more intensively using different update rates (e.g., smaller incremental weight adjustments per round) for such areas of the network.

In one example, a system that supports differential update rates as described herein includes a learning component that can determine respective weights assigned to respective node inputs of a learning network in accordance with a learning phase of the learning network. The learning network can be a neural network, for example, having a plurality of nodes and associated node inputs. A differential rate component can apply one update rate to adjust weights assigned to one of the respective node inputs while applying different update rates across different portions of the network, if desired. Different update rates can be applied, for example, based on segmentations of a training data set, segmentations of network nodes, and/or based on identifying designated features of a training data set such as noise and/or depth detected in image data, for example. As different update rates are applied across different portions of the network in accordance with the learning phase, different evaluation functions (e.g., error loss functions) can be respectively associated with the respective differential weighting to facilitate determination of the effects of the respective differential rates as applied across different portions of the network. Although, various application examples are illustrated and described herein (e.g., Medical Image Analysis, Data Classification) substantially any type of learning network application that operates in accordance with differential update rates can also be employed.

FIG. 1 illustrates an example system 100 that employs differential update rates to facilitate learning and performance of a learning network component 110, in accordance with one or more examples of the disclosed subject matter. The system 100 can include a memory 114 configured locally and/or remotely across a communications network (not shown) that can store computer-executable components as described herein. A processor 120 (or processors—executing locally and/or remotely) can be operably coupled to the memory 114 and can execute the computer-executable components stored in the memory as described herein. The computer-executable components can include a learning component 130 that can determine respective weights, using variable separator component 132, assigned to respective node inputs (including input nodes and intermediate nodes) of the learning network component 110 in accordance with a learning phase of the learning network component.

The weights can be adjusted (e.g., incremented/decremented by a numerical value) by the learning component 130 and are depicted respectively as W1, W2, though WM, with M representing a positive integer. As used herein, the term learning phase describes a processing period where node inputs of the learning network component 110 are assigned weights which describe relevance of a respective node input's value is to the output prediction of the network at output 134 given a set of training data (see e.g., FIGS. 2, 6). The weights W1-WM can be incrementally adjusted by the learning component 130 per algorithmic and/or statistical rate computations in accordance with the learning phase and can continue until a suitable prediction accuracy can be achieved at the output 134 of the learning network component 110. The incremental value employed to adjust the weights in accordance with the learning phase is referred to as the update rate and is also referred in some contexts as the "updation" rate. A differential rate component 140 applies at least one update rate to adjust at least one weight assigned to at least one of the respective node inputs and applies at least one other update rate to adjust the respective weight assigned to at least one other of the respective node inputs in accordance with the learning phase of the learning network component 110.

Training data (not shown) can be received at node inputs I1 through IN of the learning network component 110, with N representing a positive integer. Inputs I1-IN are passed to input nodes of the learning network component 110. Inputs nodes are typically passed to one or more intermediate layers of nodes in learning networks having respective node inputs that further process combinations of the input nodes. An example of such network nodes is illustrated and described below with respect to FIG. 5. It is noted that the term node inputs can refer to input nodes that receive the inputs I1-IN, and also refers to other nodes that are influenced directly and/or indirectly in response to data supplied to the respective input nodes I1-IN. Respective nodes (input or otherwise) of the learning network component 110 can be associated with at least one input that is weighted by the learning component 130 in accordance with the learning phase described herein. Input data (e.g., from training data) can be passed to the differential rate component 140 to identify portions of the training data that are to be trained according to differential update rates as described herein.

The learning network component 110 can be a neural network component, in one example (see e.g., FIG. 2), that generates output predictions based on received node inputs that can be weighted in accordance with the learning phase of the learning network component 110. For example, training data can be provided as inputs to neural network components in accordance with the learning phase. The training data can also be applied to neural network components for data classification of a data set, where the training data can be employed by the learning component 110 to determine the respective weights associated with the respective node inputs. The weights W1-WM describe a relevance of the inputs for the data classification of the data set, where the update rate applied by the differential rate component 140 can provide an adjustment to the respective weights of the respective node inputs in accordance with the learning phase of neural network components.

As will be shown and described below with respect to FIG. 2, the learning component 130 can include a loss function component that receives prediction output data 134 from neural network components in accordance with the learning phase, where the prediction output data can be generated as feedback in response to the respective differential update rates applied by the differential rate component 140 to adjust the respective weights in accordance with the learning phase. In one example, the system 100 can be provided as a diagnostic learning network that is trained via medical image training data in accordance with the learning phase described herein (see e.g., FIG. 6). For instance, the learning component 130 can be employed to train the diagnostic learning network component 110 to facilitate prediction of a medical condition associated with medical image input data received subsequent to the learning phase.

Other training and classification examples are possible in addition to image diagnostics described herein. Some of these examples are further described infra with respect to FIG. 10 and the discussion related thereto.

As mentioned supra, various application examples are illustrated and described herein (e.g., Medical Image Analysis, Data Classification). It is to be appreciated however that substantially any type of learning network application that operates in accordance with differential update rates can also be employed. Although it is not possible to describe all such examples existing now or in the future, a few examples of machine learning applications that can operate in accordance with the learning networks described herein can include but are not limited to data classification, data segmentation, data transformation, data detection, data generation, data regression, language generation, machine translation, and sentiment analysis, for example.

Figure 2:
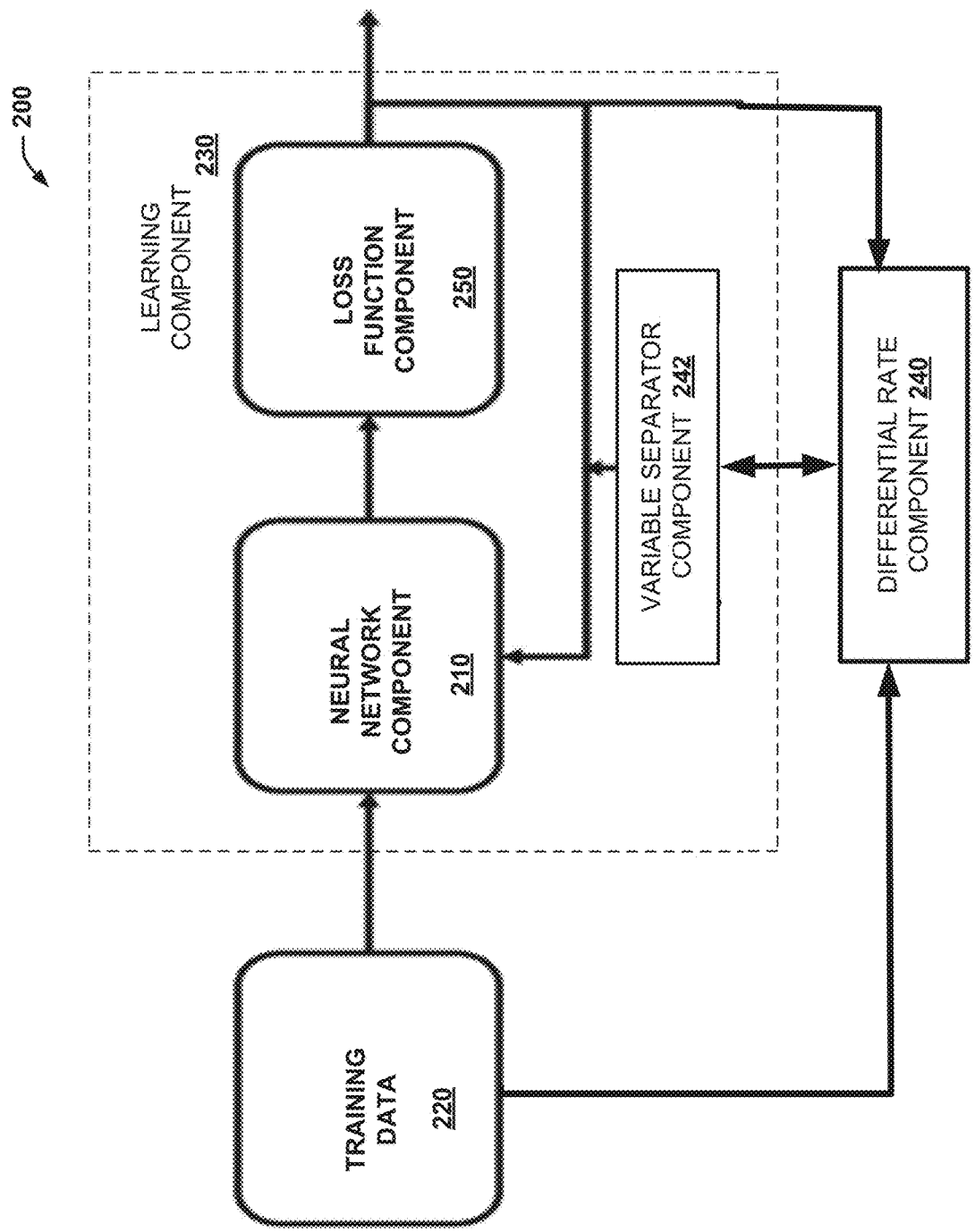
FIG. 2 illustrates a block diagram of an example system that employs differential update rates to facilitate learning and performance of a neural network component, in accordance with one or more examples of the disclosed subject matter.

FIG. 2 illustrates an example system 200 that employs differential update rates to facilitate learning and performance of a neural network component 210, in accordance with one or more examples of the disclosed subject matter. In this example, the learning network 110 described above with respect to FIG. 1 can be provided as the neural network component depicted in the system 200. The neural network component 210 can receive training data 220 which can be segmented such as illustrated and described below with respect to FIG. 6, where the data segmentation can be employed to support some of the differential learning examples described herein. A learning component 230 can include a differential rate component 240 that can apply differential update rates to weights in accordance with a learning phase such as previously mentioned with respect to FIG. 1. Based on suitable training of the neural network component 210 as described herein (e.g., based on a desired prediction accuracy threshold), the learning component 230 can be disabled.

To separate training data such that different update rates can be applied in accordance with a training phase, a variable separator component 242 can separate network weights into separate groups for applying different update rates. Different update rates can be applied to separate network weights that can facilitate determination of a correlation based on an error term E and network weights. For example, the differential update rates can be determined based on the error term E to learn multi-modal data (or other data types).

As shown, the learning component 230 can include a loss function component 250 that can receive prediction output data from the neural network component 210 in accordance with the learning phase, wherein the prediction output data can be generated in response to the respective differential update rates applied by the differential rate component 250 to adjust the respective weights in accordance with the learning phase. The loss function component 250 can compute an error term (E) associated with a given weight (W), wherein the error term E and the given weight W can be associated with an error function (f) that describes an amount of error between a predicted output ý of the neural network component 210 versus a desired output y of the neural network component at a selected update rate (n) that is applied by the differential rate component 240 in accordance with the learning phase. In a mathematical example, the differential rate component 240 can apply different update rates to the node inputs of the neural network component 210 based on the training data 220 according to the following differential rate update equations:

$$\frac{dE}{dW_1}, \frac{dE}{dW_2}, \ldots \ldots = n_1 f(y, \dot{y}), n_2 f(y, \dot{y}), \ldots \ldots$$

$$\frac{dE_1}{dW_1}, \frac{dE_2}{dW_2}, \ldots \ldots = n_1 f(y_1, \dot{y}_1), n_2 f(y_2, \dot{y}_2), \ldots \ldots$$

$$\frac{dE_1}{dW_1}, \frac{dE_2}{dW_2}, \ldots \ldots = n_1 f(y_{a \to b}, \dot{y}_{a \to b}), n_2 f(y_{b \to c}, \dot{y}_{b \to c}), \ldots \ldots$$

Differential Rate Update Equations, wherein E is the error term, $W_1$ are weights assigned to one training data subset, $W_2$ are weights assigned to another training data subset, $n_1$ is the update rate for $W_1$ and $n_2$ is the update rate for $W_2$, f is the error function ( ), y is the desired output of the neural network component, and ý is the predicted output of the neural network component. Further example mathematical description of differential rate component 240 functionality and the loss function component 250 is provided in accordance with FIG. 10 and the associated discussion related thereto. Although two example derivative weight and associated loss evaluation functions are depicted in the above equations, it is to be appreciated that the depicted series of derivative mathematical examples can be extended to a plurality of such differential weightings and associated error computations as is generally encountered in accordance with the learning phase described herein and as applied to the neural network component 210.

Figure 3:
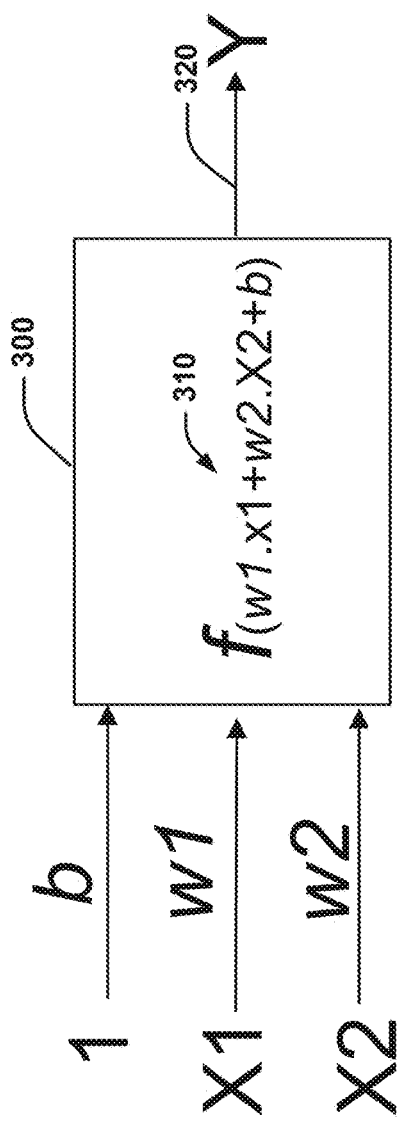
FIG. 3 illustrates an example of a neural network neuron that can employ differential update rates in accordance with a learning phase and in accordance with one or more examples of the disclosed subject matter.

FIG. 3 illustrates an example of a neural network neuron 300 that can employ differential update rates in accordance with a learning phase and in accordance with one or more examples of the disclosed subject matter. In this example, although the neuron is depicted as a rectangle, in other familiar contexts to computer scientists, neurons are often depicted as circles or bubbles. In this example, a neural network such as described above with respect to FIG. 2 can be implemented as having at least one neuron 300 that executes an activation function 310, where the neuron can receive weighted inputs X1 and X2 in this example related to image variables (e.g., image feature parameters such as from stored medical images) and can generate an output that indicates learned patterns from the respective image variables.

Figure 4:
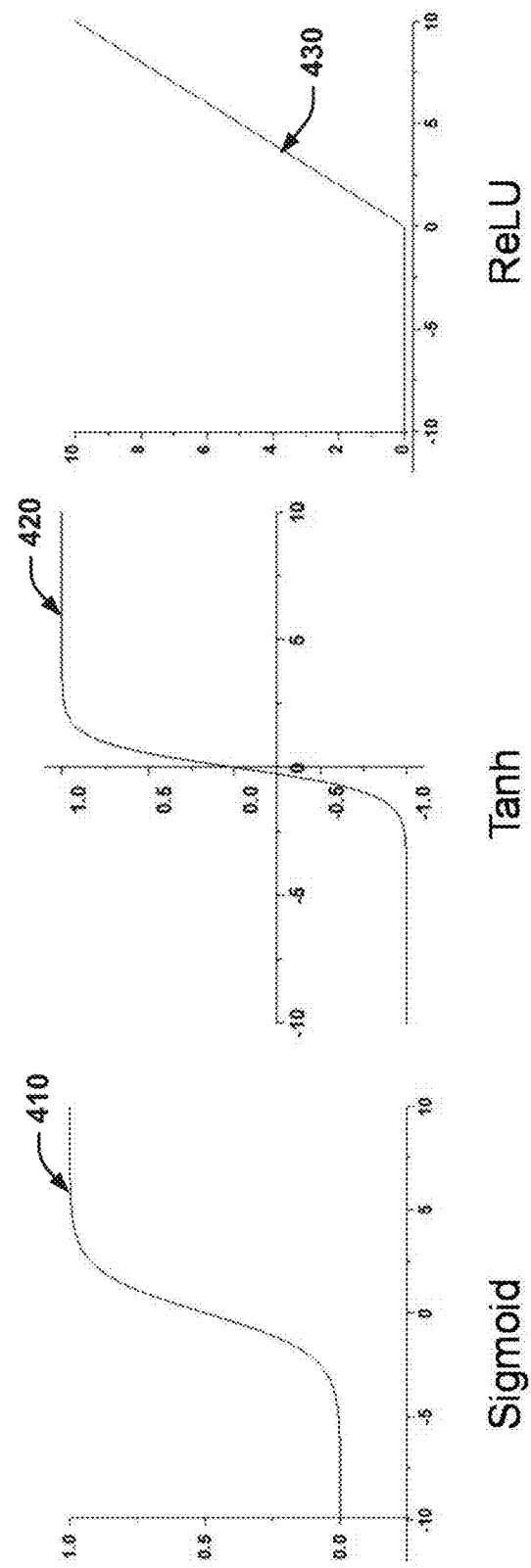
FIG. 4 illustrates activation function examples for neural network neurons that can employ differential update rates in accordance with a learning phase and in accordance with one or more examples of the disclosed subject matter.
Figure 5:
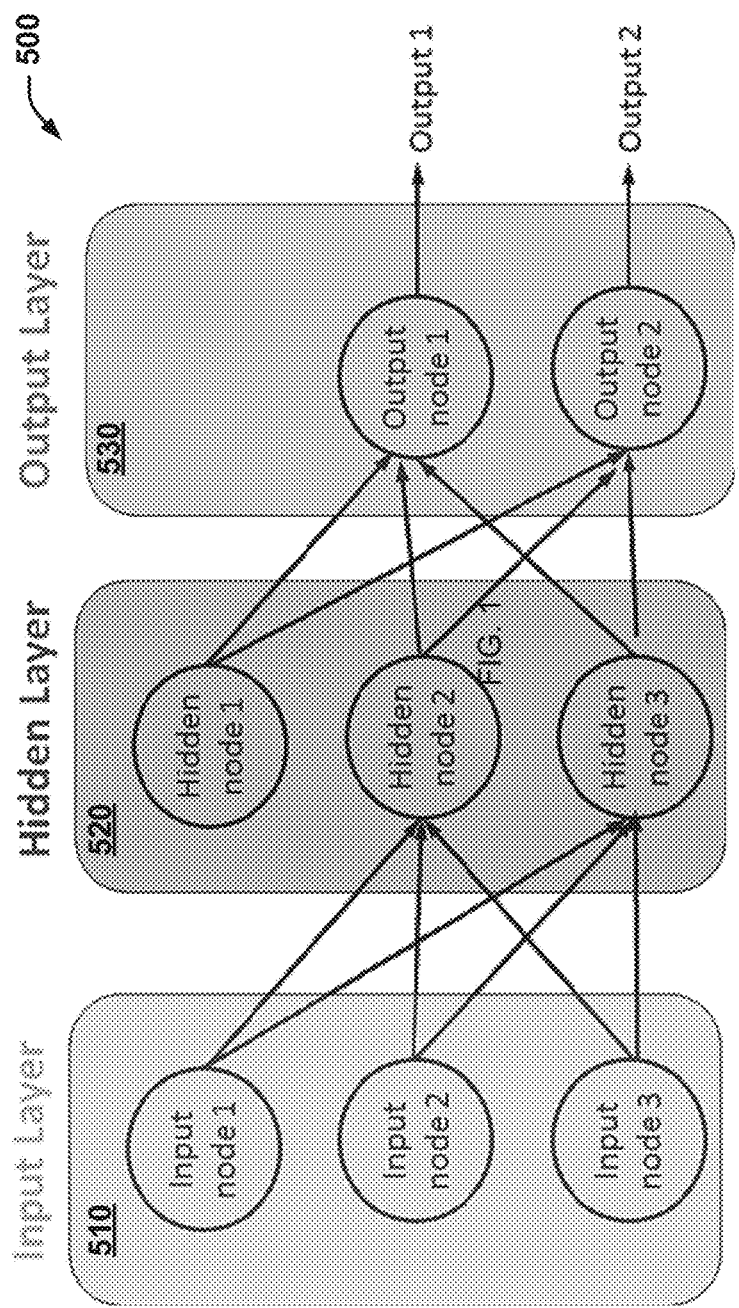
FIG. 5 illustrates an example neural network component that can employ differential rate updates in accordance with a learning phase and in accordance with one or more examples of the disclosed subject matter.

As is common, a neural network can typically be composed of a plurality of neurons such as shown and described with respect to the example network illustrated in FIG. 5. In this example, the neuron 300 can receive numerical inputs X1 and X2 and be associated with weights w1 and w2 that are respectively associated with such inputs. Additionally, there can be another input 1, for example, having associated weight b (referred to as Bias) associated with it. Output Y at 320 from the neuron 300 can be computed as shown in FIG. 4 below via example activation functions. The function f can be non-linear and can be referred to as the activation function. An example employment of the activation function is to introduce non-linearity into the output of the neuron 300.

FIG. 4 illustrates activation function examples for neural network neurons such as depicted in FIG. 3 above that can employ differential update rates in accordance with a learning phase and in accordance with one or more examples of the disclosed subject matter. At 410, a Sigmoid can receive a real-valued input and can compress the received input to an output range such as between about 0 and 1, for example. At 420, a tan h activation function can receive a real-valued input and can compress the received input to an output range of about [−1, 1], for example. At 430, a ReLU function, where ReLU stands for Rectified Linear Unit and can receive a real-valued input and threshold the input at about zero value or above (e.g., replaces negative values with zero). Examples of a Sigmoid, tan h, and ReLU are shown respectively below in Equation examples A1, A2, and A3 below:

$$\sigma(X) = \frac{1}{1+e^{-x}}, \quad \text{Equation A1}$$

$$\tanh(X) = 2\sigma(2X) - 1, \quad \text{Equation A2}$$

$$f(X) = \max(0, X). \quad \text{Equation A3}$$

Figure 6:
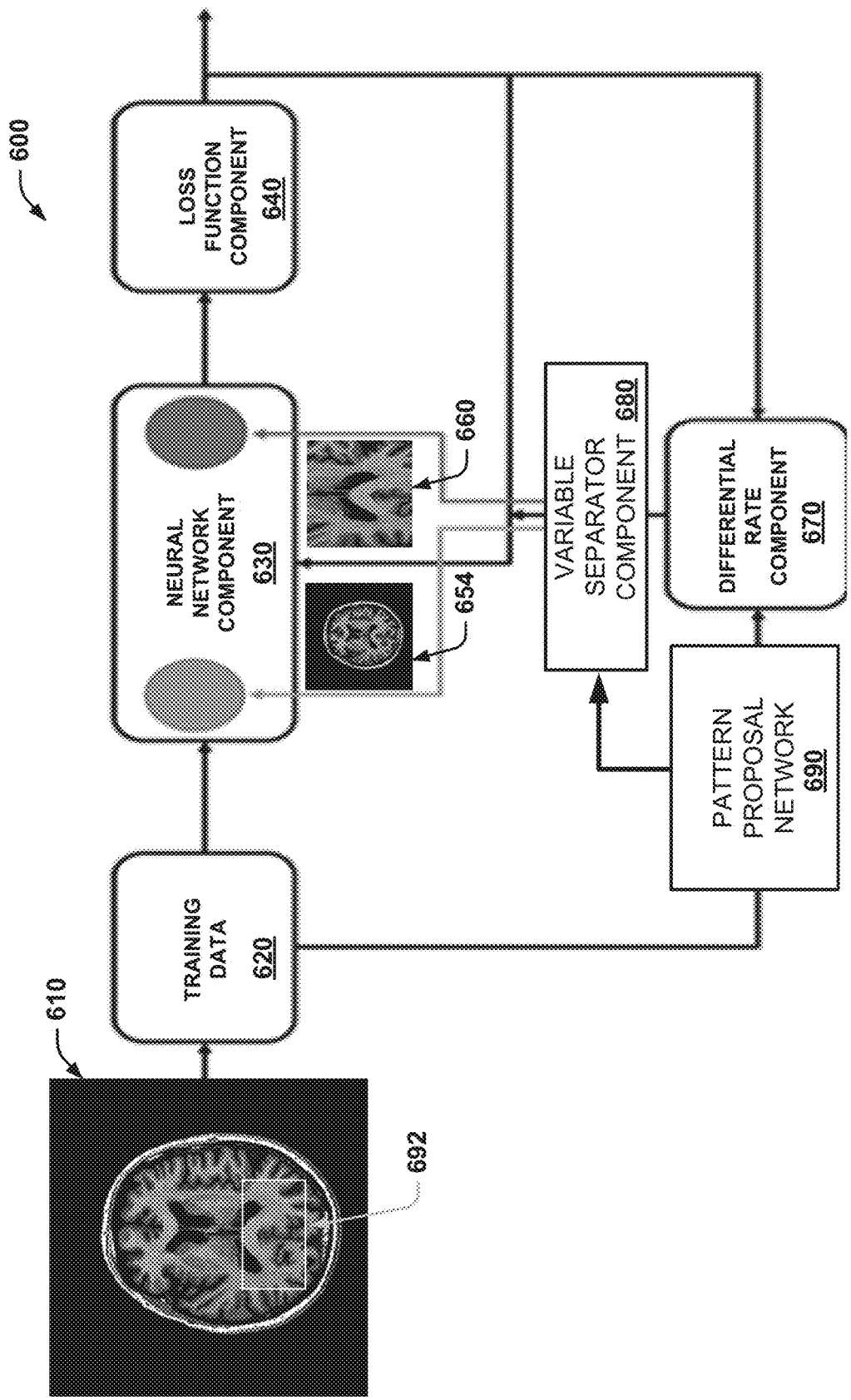
FIG. 6 illustrates a block diagram of an example variable separator system that provides image extraction to facilitate assignment of differential update rates in accordance with one or more examples of the disclosed subject matter.

FIG. 5 illustrates an example neural network component 500 that can employ differential rate updates in accordance with a learning phase and in accordance with one or more examples of the disclosed subject matter. In this example, the neural network 500 can include an input layer having one or more input nodes to receive input data relating to data such as images. A hidden layer 520 (or layers) can be connected to various learning paths from the input layer 510. An output layer 530 receives data that has been processed by the hidden layer 520 and generates one or more prediction outputs shown as Output 1 and Output 2 in this example. During the learning phase of the neural network 500, input weights applied at the input layer 510 and further processed at the hidden layer 520 can be adjusted according to their relevance in predicting the output of the network. Such weight adjustments can be determined according to differential update rates described herein, back propagation and gradient algorithms to improve neural network prediction performance. FIG. 6 illustrates an example variable separator system 600 that can provide image extraction and training data segmentation to facilitate assignment of differential update rates in accordance with one or more examples of the disclosed subject matter. The variable separator system can include an image (or a plurality of images) 610 that provide training data 620. The training data 620 is provided to a neural network component 630 to be trained, where a loss function component 640 can be employed for evaluation of the different weights applied in the training phase described herein. Example image portions 654 and 660 have differential update rates applied by a differential rate component 670. To separate the training data such that different update rates can be applied in accordance with the training phase, a variable separator component 680 and a pattern proposal network 690 can be provided. The variable separator component 680 can separate network weights into separate groups for applying different update rates generated by the differential rate component 670. As mentioned previously, the different update rates can be applied to the separate network weights that can enable a determination of a correlation based on the error term E and network weights. For example, the differential update rates can be determined based on the error term E to learn multi-modal data (or other data types). The pattern proposal network 690 can select different regions of the image 610, where the respective regions selected can include the image or portions of the image based on the selection of types of objects selected in the image. The pattern proposal network 690 can be implemented in one example as pretrained network that assists the variable separator component 680 is generally not trained while training the neural network component 630.

The pattern proposal network (PPN) 690 can be used to decide "where" to select in order to reduce the computational requirements of the overall inference process. The PPN 690 can quickly and efficiently scan respective training data image locations in order to assess whether further processing should be carried out in a given region. The PPN 690 can achieve this by outputting k bounding box proposals respectively with 2 (or more) scores representing probability of an object being present or not at the respective location.

Anchor boxes (not shown) can be employed that are references, where the boxes can be selected to have different aspect ratios and scales in order to accommodate different types of objects. Elongated objects such as blood vessels, for example, may not be properly represented by a square bounding box, where another geometrical selection type may be employed. In Faster R-CNN (Convolutional Neural Networks) the boxes can use k=9, for example representing 3 scales and 3 aspect ratios, for example. Each regressor in the PPN 690 can compute 4 offset values (w, h, x, y) to the corresponding reference anchor box, where w=width, h=height, (x,y)=center.

As an example, the PPN 690 can use a 3×3 window that slides over a high-level cony feature map, where the effective size of that smaller window can be 177×177 when re-projected back to the input layer, such that the RPN is actually using more image feature context when generating the respective proposals. This 3×3 window can be resampled to a 256 dimensional vector, for example, before feeding into two fully connected layers, a box regression layer (reg), that computes the box offsets, and the box classification layer (cls) that computes the confidence scores that are related to probability of objectness. The reg layer can have 4k (k representing thousand) outputs while the cls layer can have 2k outputs making the total PPN output per position to 4k+2k. Thus, at each location of the cony layer, for example, the bounding box regression heads outputs the bounding box offsets for each anchor box while the classification layer outputs confidence scores that represents whether an object is present or not within each anchor box. The respective boxes with a corresponding high probability of object being present can be further processed. Thus, the final proposals at each respective location can be the anchor boxes plus the box offsets with a high probability of containing an object.

In an embodiment, the system 600 can employ differential update rates according to segmented image data sets in accordance with one or more examples of the disclosed subject matter. For example, a brain image (or other medical image) (e.g., MRI, CT, X-Ray, Ultrasound, and the like) and extracted feature segment 692 can be segmented as segmented training data according to the example data separation processes described above. In this example, different update rates can be applied to the separate feature segments (or the respective image features) at 654 and 660, respectively that can also enable a determination of a spatial correlation based on the error term E between training data variables, learning rates, and/or feature spaces of the image, for example. Also, differential update rates can be determined based on the error term E to learn multi-modal data having non-uniform data complexity, wherein the multi-modal data can include at least one of noise data in the image or depth data (e.g., color or pixel intensity) in the image 610 or extracted therefrom at 692, for example. The discussion below illustrates how separate loss functions are assigned to evaluate each respective differential rate update In a related embodiment, system 600 similar can employ differential update rates and associated loss functions to evaluate segmented image data sets in accordance with one or more examples of the disclosed subject matter. With respect to the example system 600, for each respective differential update rate applied at 654 and 660, a separate loss function can be associated at 654 and 660 to evaluate respective node input affected by different weight updates described herein that are updated per each round or batch of training as described herein. For example, if four different subsets of nodes were trained according to four different update rates, then in a specific example of four as described herein, four different loss functions would be assigned to evaluate the weights applied to the respective four node subsets. Thus, a separate loss function can be instantiated for evaluating respective differential rate weight update segments to train a given learning network component as described herein. Further example mathematical description for providing differential update rates and associating respective loss functions for learning network evaluation in accordance with training is discuss infra with respect to FIG. 8.

It is to be appreciated that the term "pattern" in the pattern proposal network 490 is merely descriptive and is not intended to be limited to any specific embodiment. For example, in certain embodiments the pattern proposal network 690 can be employed in connection with various techniques to enable different task specific trainings. For example, in an embodiment the pattern proposal network 690 can be implemented in a detection task as a region (detection) proposal network. In another embodiment, the pattern proposal network 690 can be implemented in a segmentation task as a segment proposal network. In yet another embodiment, the pattern proposal network 690 can be implemented in a classification task as a class proposal network, and the like.

Figure 7:
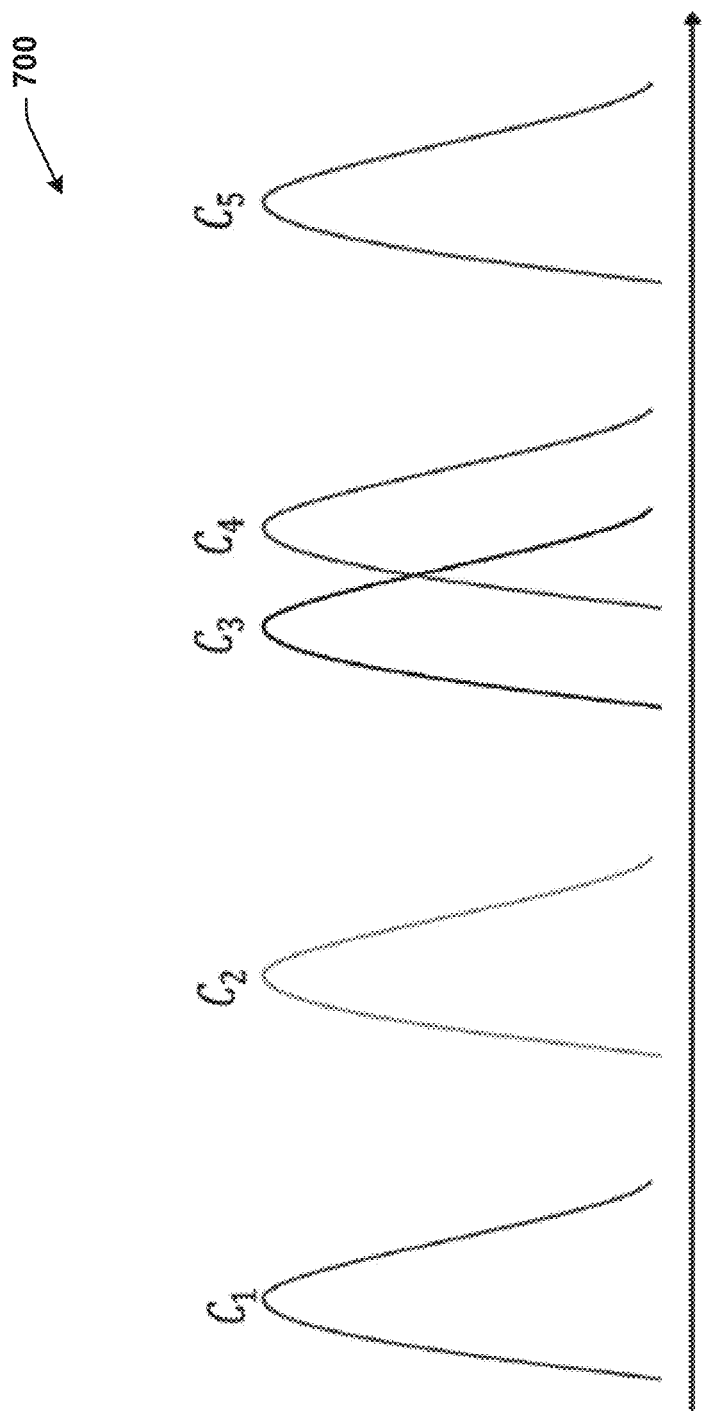
FIG. 7 illustrates an example diagram of a class distribution structure where differential update rates can be applied in accordance with one or more examples of the disclosed subject matter.

FIG. 7 illustrates an example diagram 700 of a class distribution structure where differential update rates can be applied in accordance with one or more examples of the disclosed subject matter. As discussed supra, differential learning can provide different learning rates that can employ different criteria, for example, based on individuals. Such learning can be based on distribution learning and/or ability to establish differences between individual representations, for example. Previous systems/methods operated on the summation of all the possible errors, thus potentially nullifying different minute details of a given task at hand. For instance, curriculum learning operates on learning similar types of categorization for respective batches, thus propagating weights, that can be considered as difficult by respective models. This can be achieved through inference and/or being labeled as difficult samples. However, when updating the weights employing via conventional techniques (e.g., uniform update rates mentioned supra), that is—the same learning rate applied to all weights considered in a respective learning phase, then learning time performance can suffer along with inadequate training of the network as mentioned supra.

The subject examples described herein can solve these uniform rate deficiencies by the differential learning rates described herein, where different update rates and associated error rates can be applied for different parts of the network, and thus improve future inference capability and/or mitigate learning phase time. This innovative concept is based in part in that different parts of the learning network can be triggered and/or utilized to learn a respective distribution also to facilitate generating a respective inference therefrom. FIG. 7 and the associated discussion provides other non-limiting examples of learning techniques that can enable different applications that can employ differential learning as described herein. These techniques can be illustrated in part by referring to FIG. 7, through mathematical equations related to FIG. 7 and differential learning, and also, to other non-limiting examples associated therewith that can illustrate in part such differential learning innovations.

Considering the distribution of n classes $\{C_1, C_2, \ldots, C_n\}$ depicted in the diagram 700 for classifications, some example description of a multi-class problem for which differential learning can be applied is provided. Here, a non-overlapping class distribution depicted as class distributions C1, C2, and C5 in the diagram 700 can be learned as well apart from the individual distribution, while the overlapping distributions depicted as class distributions C3 and C4 be learned for establishing differences between overlapping and non-overlapping distributions. While, previous classification systems can learn both overlapping and non-overlapping distributions, they often avoid individual caring for improvement, and thus, that can result in improper learning and confusion that can be burdensome for similar types of classes.

Mathematically, the updation of learn-able weights as practiced by conventional techniques can be represented as the following equation 2, $$\frac{\partial E}{\partial w} = \Sigma \eta f(y, \hat{y}), \quad \text{(Equation 2)}$$

where y is the ground truth and $\hat{y}$ is the estimated prediction for $\{x, y\}$ pair. But as conventional techniques estimate, they fail to separate out the individual effects of the different classes, resulting in the same updation rates for all weights. For example, in existing curriculum learning, a similar uniform strategy is considered where a batch (e.g., consisting of similar class samples) are used for updation of weights. As mentioned supra, uniform updation techniques can have serious flaws. The end effect can be that both class $C_i$ and class $C_j$ can have the same misclassification effects on the weights, unless the learning rate varied as disclosed herein, which is a current defect in curriculum learning, for example. Thus, a "one-size-fits-all" updation rate strategy employed in the respective learning phase by prior techniques, systems, and methods, can be overcome by the differential updation techniques described herein. For example, by observing Equation 1, how can a given network differentiate that whether the gradient is for class $C_i$ or for class $C_j$ and how will the updation will be differentiated. This is a serious deficiency of curriculum learning and/or other learning techniques.

To illustrate an example of the differential rate techniques mentioned supra, a differential error gradient $\Phi(.)$ can be defined with the following equation 3.

$$\Phi(y, \hat{y}) = \left[ \frac{\partial E_1}{\partial w}; \frac{\partial E_2}{\partial w}; \frac{\partial E_3}{\partial w}; \ldots; \frac{\partial E_n}{\partial w} \right], \quad \text{(Equation 3)}$$

where the function $\Phi(.) \in \mathbb{R}^n$ can be assigned with the matrix $$\left[ \frac{\partial E_1}{\partial w}; \frac{\partial E_2}{\partial w}; \frac{\partial E_3}{\partial w}; \ldots; \frac{\partial E_n}{\partial w} \right]$$

for different updates of respective weights, where the role of $\Phi(.)$ provides a differential updation of weights as individual error components are respectively propagated.

If a set of m variables $W \in \mathbb{R}^m$ are considered, and updates from $\Phi(.)$ are considered, a learning rate can be defined as $N \in \mathbb{R}^m$ for W as the $N_w$, $$N = N_W = M\Phi(y, \bar{y}) \quad \text{Equation 4,}$$

where $M \in \mathbb{R}^{m \times n}$ is defined as the monitor matrix, which can determine which information a given variable should learn. This is unlike conventional learning rate techniques where the same $\eta$ is employed for respective variables. Also, other complex problems can be solved, that consider differentiability of error. Thus, non-differentiable example functions such as Relu, Leaky-Relu and the like can be employed. An error criteria can be defined with $\Phi(.)$ such as, $$\Phi(y, \hat{y}) = [\eta_{C_1} \Sigma f(y_{C_1}, \hat{y}_{C_1}); \ldots ; \eta_{C_n} \Sigma f(y_{C_n}, \hat{y}_{C_n})]. \quad \text{(Equation 5)}$$

With cross-entropy, the above equation 4 can be defined as the following:

$$\Phi(y, \hat{y}) = [\eta_{C_1} \Sigma \log(\hat{y}_{C_1}); \ldots ; \eta_{C_n} \Sigma \log(\hat{y}_{C_n})], \quad \text{(Equation 6)}$$

Considering that network division strategy for updation as disclosed herein for both overlapping and/or non-overlapping distributions, the following constraints can also be defined for a non-sharing network, $$N = M_{ns}\Phi(y, \hat{y}) \quad \text{Equation 7,}$$

With partial sharing of the network for updation, the following equation can be defined as, $$N = M_{ps}\Phi(y, \hat{y}) \quad \text{Equation 8,}$$

where constrained monitor matrixes can be defined as $M_{ns}$ and $M_{ps}$ for the overlapping and non-overlapping distributions, respectively.

Conventional updation procedures can be mathematically represented as the following, $$W_t = W_{t-1} + \eta \frac{\partial E}{\partial W} = W_{t-1} + \begin{bmatrix} \eta \\ \eta \\ \vdots \\ \eta \end{bmatrix} \begin{bmatrix} \frac{\partial E}{\partial W} \\ \frac{\partial E}{\partial W} \\ \vdots \\ \frac{\partial E}{\partial W} \end{bmatrix}. \quad \text{(Equation 9)}$$

Whereas, the differential rate-based update as described herein can be represented as the following equation, $$W_t = W_{t-1} + M_{pn}\Phi(y, \hat{y}) = W_{t-1} + \begin{bmatrix} \eta_1 \\ \eta_2 \\ \vdots \\ \eta_n \end{bmatrix}. \quad \text{(Equation 10)}$$

While, the respective gradient can be derived from different equations as a function expected outcomes, two non-limiting examples are provided that illustrate different situations where two types of problems are considered. One problem persists to the learning of the distribution (e.g., the prior of the distribution of the data) and the other problem is related to learning the difference in distribution (features that differentiate them). Individual classification based error gradient can facilitate in identification of respective weights that can learn to minimize the class distribution Confusion Matrix described herein.

Equation 4 and Equation 5 can be employed for individual classification, whereas the gradient can be derived from the individual class based misclassification. However, in several situations, learning individual distribution may not be enough and thus the differential rate techniques described herein can facilitate improved inference.

The Confusion Matrix $C_m$ can be employed for gathering the respective gradient and can be defined as the following, $$\Psi(C_M) = [\eta_{1,2}\Sigma(y \neq \hat{y})_{1 \to 2}; \ldots ; \eta_{(n-1) \to n}\Sigma(y \neq \hat{y})_{(n-1) \to n}] \quad \text{Equation 11,}$$

where $(y \neq y)_{(n-1) \to n}$ can define the samples in class $C_{(n-1)}$ misclassified as class $C_n$. Also, while if considering the cross entropy of the confused sample likelihood, the following equation provides, $$\Psi(C_M) = [\Sigma\eta_{1,2}\log(\hat{y}_{1,2}); \ldots ; \Sigma\eta_{n-1,n}\log(\hat{y}_{n-1,n})], \quad \text{Equation 12,}$$

where $C_M \in \mathbb{R}^{(n \times n)/2}$, $\Psi(.)$ provides an example of confusion matrix content based differential error gradient.

Considering the classification problem for classes $\{C_1, C_2, \ldots, C_n\}$ of diagram 700 as a maximization of the individual likelihood and the discussion examples related thereto, similar concepts can be considered for different application example, but not limited thereto, that can include classification, computer vision, reinforcement learning, natural languages, and the like.

An example of facial recognition can be considered. For instance, face classes $\{C_1, C_2, \ldots, C_n\}$ can be considered and thus, can be classified. Using Equation 3 for example, a learning network can be trained such that for each respective class $C_i$ error can be propagated through $\Phi(yc_i, \hat{y}c_i)$. After a desired amount of training, if it is found that $C_i$ is confused with $C_j$, in that case, the gradient expressed in Equation 10 can be employed to learn differences in distribution and also establish parameters for sensitive differentiation between different facial classes, in this non-limiting example.

For instance, if there are 4 classes in this example, a gradient can be established for the four classes. Consider a batch size of 40, for example, where there are 12 from classes $C_1$, 8 from class $C_2$, 15 from class $C_3$ and 5 from class $C_4$. Out of 12 in class $C_1$, where 6 were misclassified. Similarly, for class $C_2$, 4 were misclassified, for class $C_3$ 12 were misclassified and 2 were misclassified.

So the misclassification ratio can be expressed as the following.

$$B = \begin{bmatrix} \text{total} & \text{error} & \text{ratio} \\ 12 & 6 & 0.5 \\ 8 & 4 & 0.5 \\ 15 & 12 & 0.8 \\ 5 & 2 & 0.4 \end{bmatrix}. \quad \text{(Equation 13)}$$

The gradient matrix can thus be denoted as the following, $$\Phi(y, \hat{y}) = \begin{bmatrix} 0.5 \\ 0.5 \\ 0.8 \\ 0.4 \end{bmatrix}. \quad \text{(Equation 14)}$$

For example, if there are 5 variables, as the following, $$W = \begin{bmatrix} 0.01 \\ 0.001 \\ 0.002 \\ 0.04 \\ 0.0001 \end{bmatrix}.$$  (Equation 15)

A monitor matrix M, can be established as:

$$M = \begin{bmatrix} 0.9 & 0.8 & 0.1 \\ .04 & .09 & 0.35 \\ 0.8 & 0.4 & 0.5 \\ 0.15 & 0.12 & 0.8 \\ 0.5 & 0.2 & 0.4 \end{bmatrix}.$$  (Equation 16)

The updation rate for W can be expressed as the following, $$N = M\Phi(y, \hat{y}) = \begin{bmatrix} 0.9 & 0.8 & 0.1 & 0.2 \\ .04 & .09 & 0.35 & 0.03 \\ 0.8 & 0.4 & 0.5 & 0.01 \\ 0.05 & 0.12 & 0.558 & 0.88 \\ 0.05 & 0.2 & 0.0 & 0.9 \end{bmatrix} \begin{bmatrix} 0.5 \\ 0.5 \\ 0.8 \\ 0.4 \end{bmatrix},$$  (Equation 17)

(Equation 18)

$$N = M\Phi(y, \hat{y}) =$$

$$\begin{bmatrix} 0.9*0.5 + 0.8*0.5 + 0.1*0.8 + 0.2*0.4 \\ 0.04*0.5 + .09*0.5 + 0.35*0.8 + 0.03*0.4 \\ 0.8*0.5 + 0.4*0.5 + 0.5*0.8 + 0.01*0.4 \\ 0.05*0.5 + 0.12*0.5 + 0.558*0.8 + 0.88*0.4 \\ 0.05*0.5 + 0.2*0.5 + 0.0*0.8 + 0.9*0.4 \end{bmatrix} = \begin{bmatrix} 1.01 \\ 0.36 \\ 1.00 \\ 0.88 \\ 0.49 \end{bmatrix}.$$

In addition to the mathematical and/or computational examples described herein, there are other problems that can be considered and thus solve by the differential update rate techniques described herein. For instance, computer vision methods may be dependent on the regional influence of the different portions of images. To make improve such computer vision issues, the following equations provide mathematical examples where different learning rates can be applied to images (see e.g., FIG. 6). Considering that k regions in a given image can be defined as $\{R_0, R_1, R_2, \ldots, R_k\}$, then for each of the respective regions $i \in \{1, 2, \ldots, k\}$, learning rates can be defined as the following, $$\phi(R, \hat{R}) = [\eta_{R_1} \Sigma g(y_{R_1}, \hat{y}_{R_1}); \ldots ; \eta_{R_n} \Sigma g(y_{R_n}, \hat{y}_{R_n})],$$  (Equation 19)

where we have defined ∅(.) is the regional learning rate and can include an associated $g(.) \in \mathbb{R}^k$ that can provide a score—e.g., an inception score and/or pixel to pixel difference. Each of the respective image regions can have highly dedicated flow of gradients to facilitate learning different spatial relationships. The respective techniques and methods described herein can also be extended to other example applications such as image generation and/or image-to-image translation learning problems, for example.

Figure 8:
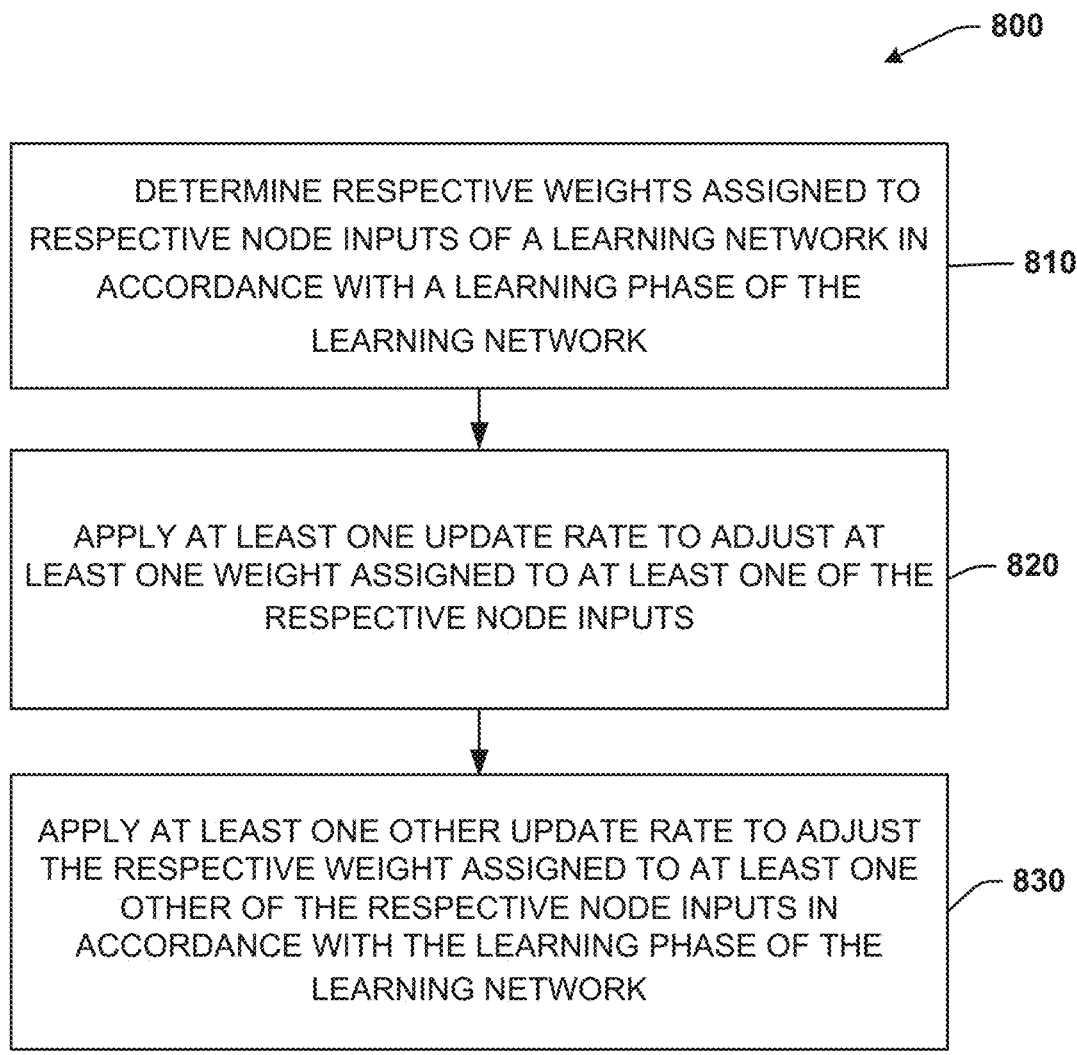
FIG. 8 illustrates a flow diagram of an example method that employs differential update rates to facilitate learning and performance of a learning network in accordance with one or more examples of the disclosed subject matter.

FIG. 8 illustrates a computer-implemented methodology 800 via flow diagram in accordance with the disclosed subject matter. For simplicity of explanation, the methodology is depicted and described as a series of acts. It is to be understood and appreciated that the subject method is not limited by the acts illustrated and/or by the order of acts, for example, acts can occur in various orders and/or concurrently, and with other acts not presented and described herein. Furthermore, not all illustrated acts may be employed to implement the methodology in accordance with the disclosed subject matter. In addition, those skilled in the art will understand and appreciate that the methodology could alternatively be represented as a series of interrelated states via a state diagram or events. Additionally, it should be further appreciated that the methodology disclosed hereinafter and throughout this specification are capable of being stored on an article of manufacture to facilitate transporting and transferring such methodologies to computers. The term article of manufacture, as used herein, is intended to encompass a computer program accessible from any suitable computer/machine-readable device and/or storage media.

Referring to FIG. 8, the example method 800 employs differential update rates to facilitate learning and performance of a learning network in accordance with one or more examples of the disclosed subject matter. At 810, the computer-implemented method 800 can include determining, by a system operatively coupled to a processor, respective weights assigned to respective node inputs of a learning network in accordance with a learning phase of the learning network (e.g., via learning component 130 of FIG. 1). At 820, the method 800 can include applying, by the system, at least one update rate to adjust at least one weight assigned to at least one of the respective node inputs (e.g., via learning component 130 and differential rate component 140 of FIG. 1). At 830, the method 800 can include applying, by the system, at least one other update rate to adjust the respective weight assigned to at least one other of the respective node inputs in accordance with the learning phase of the learning network (e.g., via learning component 130 and differential rate component 140 of FIG. 1).

The learning network in one example can be a neural network component that generates output predictions based on received node inputs that can be weighted in accordance with the learning phase of the learning network. Also, training data can be provided as the inputs to the neural network component in accordance with the learning phase, where the training data can be applied to the neural network component for data classification of a data set, and where the training data can be employed to determine the respective weights associated with the respective node inputs. The weights can describe a relevance of the node inputs for the data classification of the data set, where the respective update rate applied can provide an adjustment to the respective weights of the respective node inputs in accordance with the learning phase. Although not shown, the method 800 can include computing a loss function that receives prediction output data from the neural network component in accordance with the learning phase, where the prediction output data can be generated in response to the respective update rates applied to adjust the respective weights in accordance with the learning phase. In an example, the loss function can compute an error term (E) associated with a given weight (W), wherein the error term E and the given weight W is associated with an error function (ƒ) that describes an amount of error between a predicted output ŷ of the neural network component versus a desired output y of the neural network component at a selected update rate (n) that can be applied in accordance with the learning phase. Also, the computer-implemented method 800, can include applying different update rates to the respective node inputs described herein based on the training data and according to the differential rate update equations:

$$\frac{dE}{dW_1}, \frac{dE}{dW_2}, \ldots \ldots = n_1 \, f(y, \acute{y}), n_2 \, f(y, \acute{y}), \ldots \ldots$$

$$\frac{dE_1}{dW_1}, \frac{dE_2}{dW_2}, \ldots \ldots = n_1 \, f(y_1, \acute{y}_1), n_2 \, f(y_2, \acute{y}_2), \ldots \ldots$$

$$\frac{dE_1}{dW_1}, \frac{dE_2}{dW_2}, \ldots \ldots = n_1 \, f(y_{a \to b}, \acute{y}_{a \to b}), n_2 \, f(y_{b \to c}, \acute{y}_{b \to c}), \ldots \ldots$$

Differential Rate Update Equations, wherein E is the error term, $W_1$ are weights assigned to one training data subset, $W_2$ are weights assigned to another training data subset, $n_1$ is the update rate for $W_1$ and $n_2$ is the update rate for $W_2$, $f$ is the error function ( ), y is the desired output of the neural network component, and ý is the predicted output of the neural network component.

Figure 9:
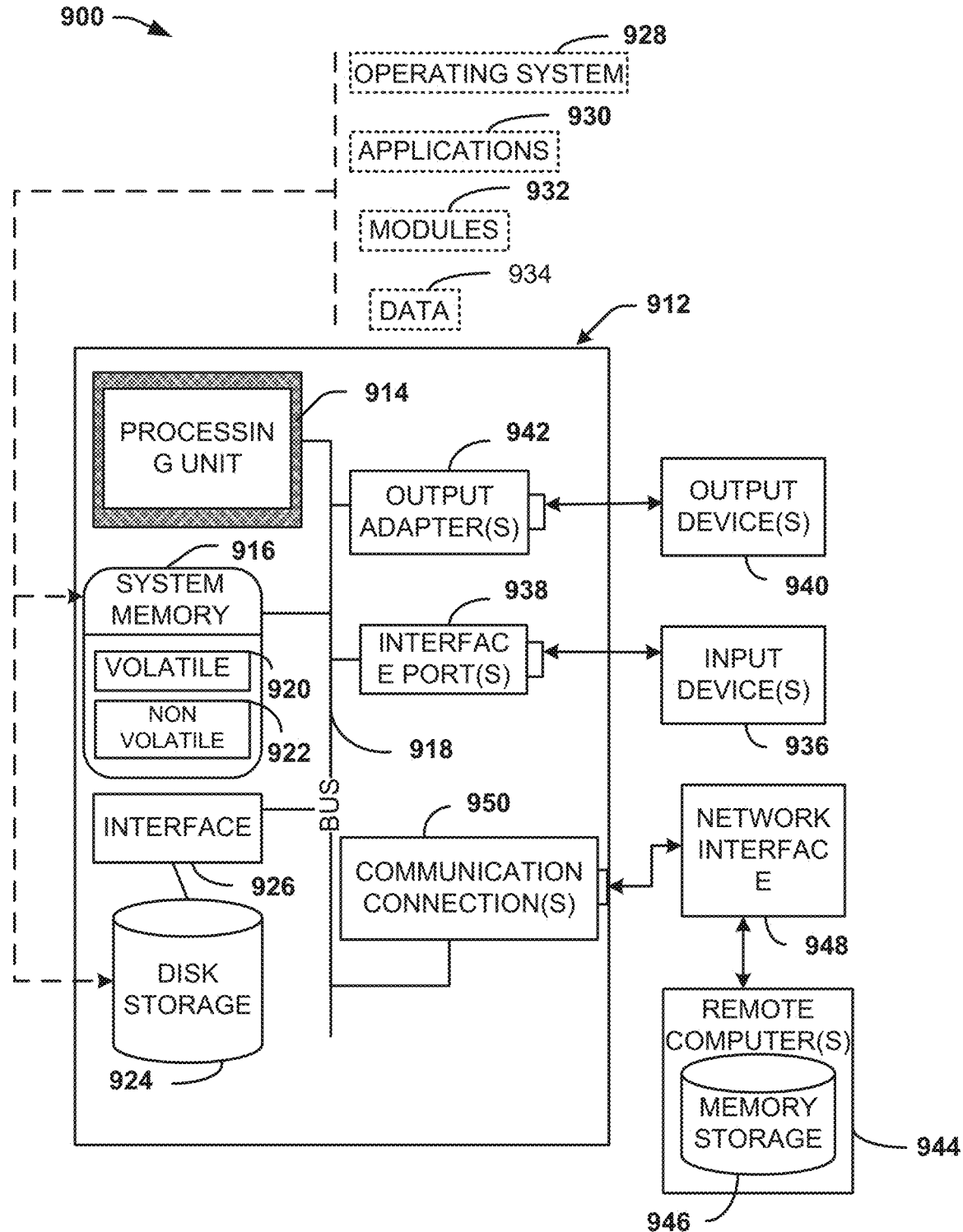
FIG. 9 illustrates a block diagram of an example, non-limiting operating environment in which one or more embodiments described herein can be implemented that can facilitate differential update rates applied in accordance with a learning phase.

FIG. 9 illustrates an example, non-limiting operating environment 900 in which one or more embodiments described herein can be implemented that can facilitate differential update rates applied in accordance with a learning phase. With reference to FIG. 9, the example environment 900 for implementing various aspects of the claimed subject matter can include a computer 902. The computer 902 can include a processing unit 904, a system memory 906, a codec 935, and a system bus 908. The system bus 908 can couple system components including, but not limited to, the system memory 906 to the processing unit 904. The processing unit 904 can be any of various available processors. Dual microprocessors and other multiprocessor architectures also can be employed as the processing unit 904.

The system bus 908 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 13154), and Small Computer Systems Interface (SCSI).

The system memory 906 can include volatile memory 910 and non-volatile memory 912, which can employ one or more of the disclosed memory architectures, in various examples. The basic input/output system (BIOS), containing the basic routines to transfer information between elements within the computer 902, such as during start-up, can be stored in non-volatile memory 912. In addition, according to present innovations described herein, a codec 935 can include at least one of an encoder or decoder, wherein the at least one of an encoder or decoder can consist of hardware, software, and/or a combination of hardware and software. Although, codec 935 is depicted as a separate component, codec 935 can be contained within non-volatile memory 912. By way of illustration, and not limitation, non-volatile memory 912 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 912 can employ one or more of the disclosed memory devices, in at least some examples. Moreover, non-volatile memory 912 can be computer memory (e.g., physically integrated with computer 902 or a mainboard thereof), or removable memory. Examples of suitable removable memory with which disclosed examples described herein can be implemented can include a secure digital (SD) card, a compact Flash (CF) card, a universal serial bus (USB) memory stick, and/or the like. Volatile memory 910 can include random access memory (RAM), which can act as external cache memory, and can also employ one or more disclosed memory devices in various examples. By way of illustration and not limitation, RAM can be provided in many forms such as static RAM (SRAM), dynamic RAM (DRAM), synchronous DRAM (SDRAM), double data rate SDRAM (DDR SDRAM), and enhanced SDRAM (ESDRAM), for example.

Computer 902 can also include removable/non-removable, volatile/non-volatile computer storage medium. FIG. 9 illustrates, for example, disk storage 914. Disk storage 914 can include, but is not limited to, devices such as a magnetic disk drive, solid state disk (SSD), flash memory card, or memory stick. In addition, disk storage 914 can include storage medium separately and/or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 914 to the system bus 908, a removable or non-removable interface can be used, such as interface 916. It is appreciated that disk storage 914 can store information related to an entity. Such information might be stored at or provided to a server (or servers) and/or to an application running on an entity device. In one example, the entity can be notified (e.g., by way of output device(s) 936) of the types of information that can be stored to disk storage 914 or transmitted to the server or application. The entity can be provided the opportunity to opt-in or opt-out of having such information collected or shared with the server and/or application (e.g., by way of input from input device(s) 928).

It is to be appreciated that FIG. 9 describes software that can act as an intermediary between entities and the basic computer resources described in a suitable such as the example operating environment 900. Such software can include an operating system 918. Operating system 918, which can be stored on disk storage 914, can act to control and allocate resources of the computer system 902. Applications 920 can take advantage of the management of resources by operating system 918 through program modules 924, and program data 926, such as the boot/shutdown transaction table and the like, stored in system memory 906 and/or on disk storage 914. It is to be appreciated that the claimed subject matter can be implemented with various operating systems and/or combinations of operating systems.

An entity can enter commands and/or information into the computer 902 through input device(s) 928. Input devices 928 can include, but are not limited to, a pointing device such as a mouse, trackball, stylus, touch pad, keyboard, microphone, joystick, game pad, satellite dish, scanner, TV tuner card, digital camera, digital video camera, web camera, and/or the like. These and other input devices can connect to the processing unit 904 through the system bus 908 via interface port(s) 930. Interface port(s) 930 can include, for example, a serial port, a parallel port, a game port, and a universal serial bus (USB). Output device(s) 936 can employ some of the same type of ports as input device(s) 928. Thus, for example, a USB port can be used to provide input to computer 902 and to output information from computer 902 to an output device 936. Output adapter 934 illustrates, in this example, that there are some output devices 936 such as monitors, speakers, and printers, among other output devices 936, which can employ dedicated adapters. The output adapters 934 can include, by way of illustration and not limitation, video and sound cards that can provide a coupling between the output device 936 and/or the system bus 908. It should be noted that other devices or systems of devices can provide input and/or output capabilities such as remote computer(s) 938, for example.

Computer 902 can operate in a networked environment using logical connections to one or more remote computers, such as remote computer(s) 938. The remote computer(s) 938 can be a personal computer, a server, a router, a network PC, a workstation, a microprocessor based appliance, a peer device, a smart phone, a tablet, and/or other network node, and can include many of the elements described relative to computer 902. For purposes of brevity, only a memory storage device 940 is illustrated with remote computer(s) 938. Remote computer(s) 938 can be logically connected to computer 902 through a network interface 942 and can then be coupled via communication connection(s) 944. Network interface 942 can encompass wired and/or wireless communication networks such as local-area networks (LAN), wide-area networks (WAN), and/or cellular networks, for example. LAN technologies, for example, can include Fiber Distributed Data Interface (FDDI), Copper Distributed Data Interface (CDDI), Ethernet, Token Ring and/or the like. WAN technologies, for example, can include, but are not limited to, point-to-point links, circuit switching networks such as Integrated Services Digital Networks (ISDN) and variations thereon, packet switching networks, and/or Digital Subscriber Lines (DSL).

Communication connection(s) 944 can link to the hardware/software employed to couple the network interface 942 to the bus 908. While communication connection 944 is shown for illustrative clarity inside computer 902, it can also be external to computer 902. The hardware/software for coupling to the network interface 942 can include, for exemplary purposes only, internal and/or external technologies such as, modems including regular telephone grade modems, cable modems, DSL modems, ISDN adapters, and/or wired and/or wireless Ethernet cards, hubs, and routers.

The illustrated aspects of the disclosure may also be practiced in distributed computing environments where desired tasks are performed by remote processing devices that can be coupled through a communications network. In a distributed computing environment, for example, program modules can be located in local and/or remote memory storage devices.

Figure 10:
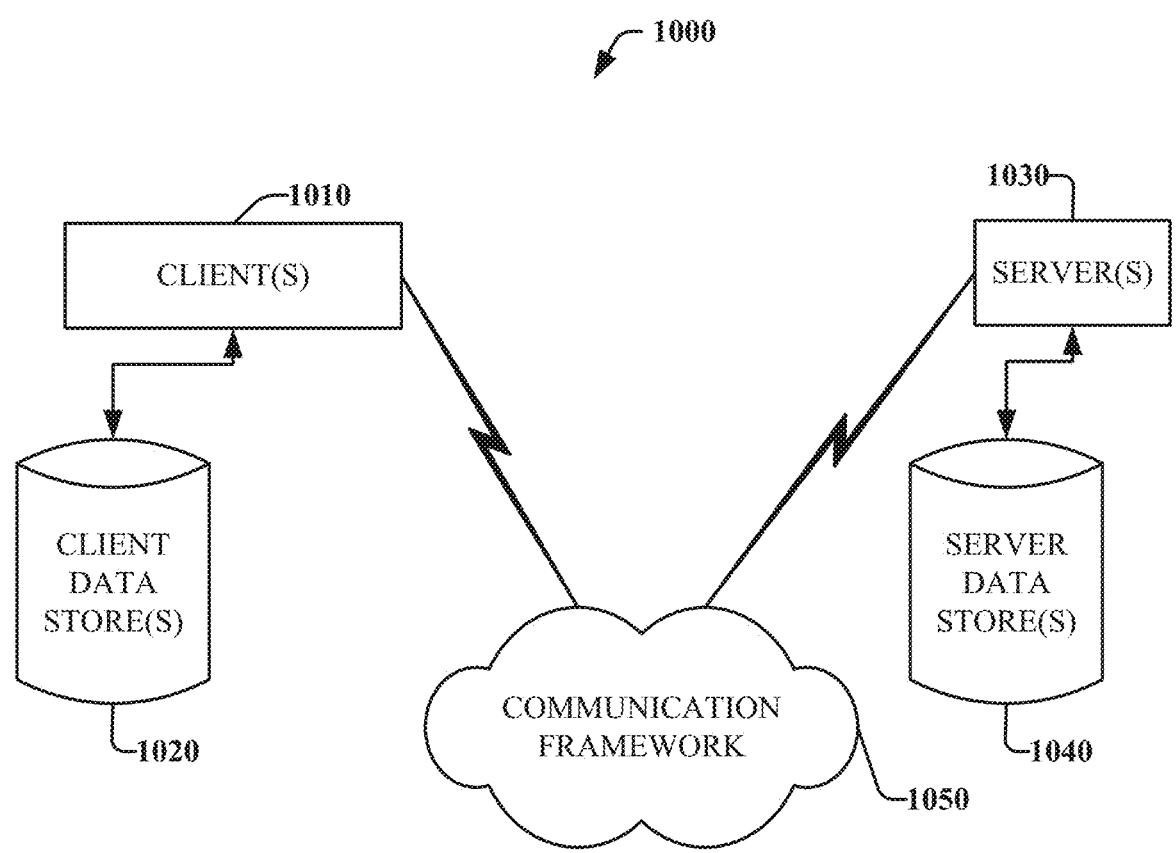
FIG. 10 illustrates a block diagram of another example, non-limiting operating environment in which one or more embodiments described herein can be implemented that can facilitate differential update rates applied in accordance with a learning phase.

FIG. 10 illustrates another example, non-limiting operating environment 1000 in which one or more embodiments described herein can be implemented that can facilitate differential update rates applied in accordance with a learning phase. Referring to FIG. 10, the computing environment 1000 is but one example to illustrate operating conditions in accordance with this disclosure in which the subject systems (e.g., systems 100, 200, 500, 600, 900, and the like), methods and computer readable media can be deployed. The computing environment 1000 can include one or more client(s) 1002 (e.g., laptops, smart phones, PDAs, media players, computers, portable electronic devices, tablets, and the like). The client(s) 1002 can be hardware and/or software (e.g., threads, processes, computing devices). The computing environment 1000 can also include one or more server(s) 1004 that can support tasks of the client(s) 1002. The server(s) 1004 can also be hardware and/or hardware in combination with software (e.g., threads, processes, computing devices, and/or the like). For instance, the servers 1004 can house threads to perform transformations by employing aspects of this disclosure, for example. In various examples, one or more components, devices, systems, or subsystems of the systems described herein, can be deployed as hardware and/or software at a client 1002 and/or as hardware and/or software deployed at a server 1004. One possible communication/coupling example between the client 1002 and a server 1004 can be in the form of a data packet transmitted between two or more computer processes wherein the data packet can include healthcare related data, training data, AI models, input data for the AI models, and/or the like. The data packet can include metadata, e.g., associated contextual information, for example. The computing environment 1000 can include a communication framework 1006 (e.g., a global communication network such as the Internet, or mobile network(s)) that can be employed to facilitate communications/couplings between the client(s) 1002 and/or the server(s) 1004.

Communications can be facilitated via a wired (including optical fiber) and/or wireless technology. The client(s) 1002 can include and/or can be operatively coupled to one or more client data store(s) 1008 that can be employed to store information local to the client(s) 1002 (e.g., associated contextual information). Similarly, the server(s) 1004 can include and/or can be operatively coupled to one or more server data store(s) 1010 that can be employed to store information local to and/or remote the servers 1004.

In one non-limiting example, a client 1002 can transfer an encoded file, in accordance with the disclosed subject matter, to server 1004. Server 1004 can store the file, decode the file, and/or transmit the file to another client 1002 (and/or clients). It is to be appreciated, that a client 1002 can also transfer uncompressed/compressed files to the server 1004, where the server 1004 can compress/decompress the respective file in accordance with the disclosed subject matter. Likewise, server 1004 can encode/decode video/audio information and/or can transmit/receive information via communication framework 1006 to/from one or more clients 1002.

Figure 11:
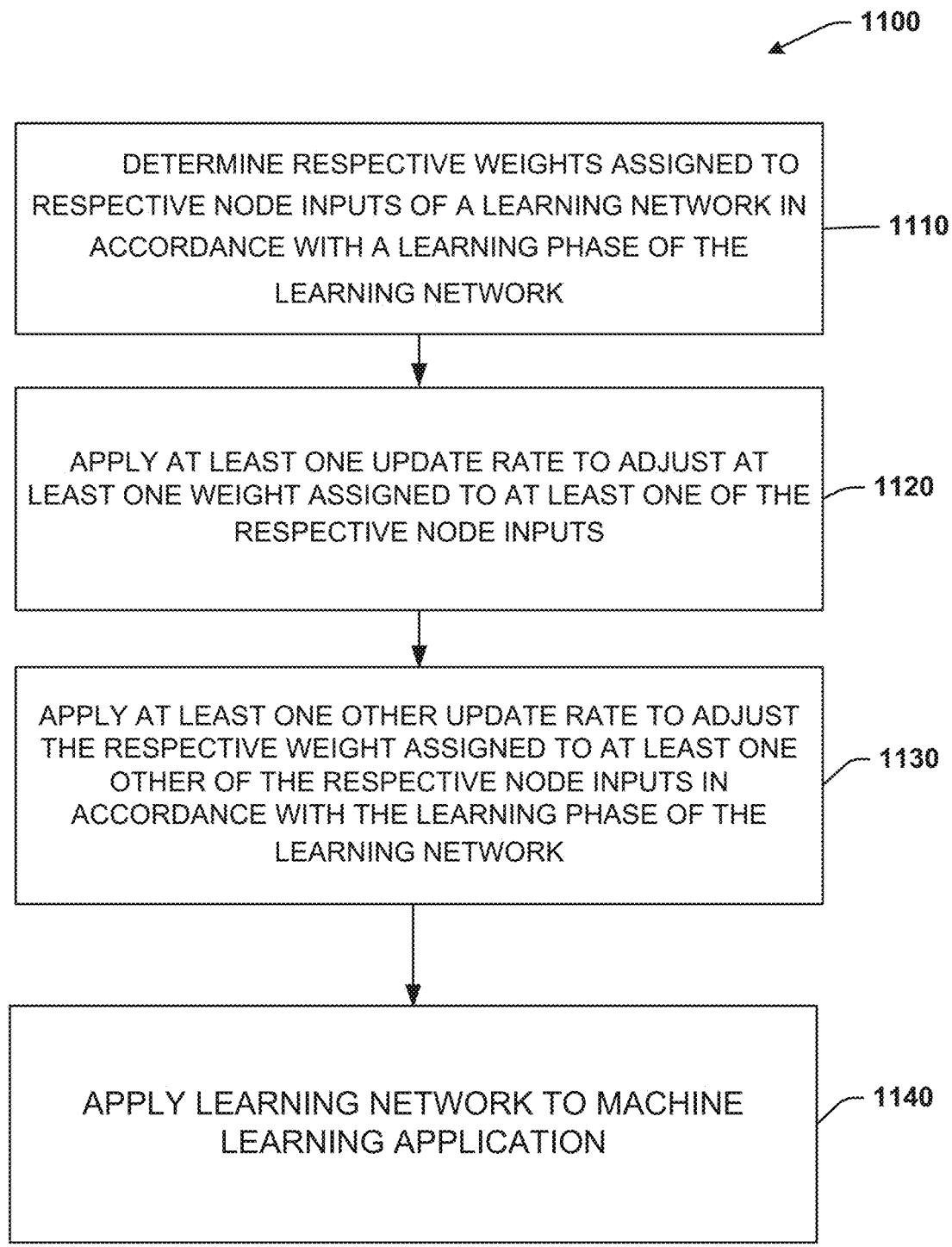
FIG. 11 is a flow diagram of an example method that employs differential update rates to facilitate learning and performance of a learning network as applied to a machine learning application in accordance with one or more examples of the disclosed subject matter.

Referring to FIG. 11, an example method 1100 employs differential update rates to facilitate learning and performance of a learning network as applied to a machine learning application in accordance with one or more examples of the disclosed subject matter. At 1110, the computer-implemented method 1100 can include determining, by a system operatively coupled to a processor, respective weights assigned to respective node inputs of a learning network in accordance with a learning phase of the learning network. At 1120, the method 1100 can include applying, by the system, at least one update rate to adjust at least one weight assigned to at least one of the respective node inputs. At 1130, the method 1100 can include applying, by the system, at least one other update rate to adjust the respective weight assigned to at least one other of the respective node inputs in accordance with the learning phase of the learning network. At 1140, the method 1100 can include applying the learning network (e.g., neural network component 210 of FIG. 1, neural network component 630 of FIG. 6) to a machine learning application. As mentioned supra, machine learning applications can include that substantially any type of learning network application that operates in accordance with differential update rates. Although it is not possible to describe all such examples, a few examples of machine learning applications that can operate in accordance with the learning networks described herein can include but are not limited to data classification, data segmentation, data transformation, data detection, data generation, data regression, language generation, machine translation, and/or sentiment analysis, for example.

One or more embodiments of the subject disclosure describes utilizing machine learning systems to apply differential update rates as described herein. Embodiments described and claimed herein can utilize machine learning systems that have been explicitly and/or implicitly trained to learn, determine and/or infer based on differential learning as described herein. This can include dynamically applying differential update rates to facilitate learning. For example, and as will be described in greater detail below, these are some of the many factors that can be taken into consideration by the machine learning systems in connection with differential update rates to achieve improved processing speeds and predictive performance as described supra.

The subject disclosure is directed can be applied to computer processing systems, computer-implemented methods, apparatus and/or computer program products that facilitate efficiently and automatically (e.g., without direct human involvement). Humans are also unable to perform the embodiments described here as they include, and are not limited to, performing, e.g., complex Markov processes, Bayesian analysis, or other artificial intelligence-based techniques based on probabilistic analyses and evaluating electronic information derived from learning, determining whether countless multitudes of probability values assigned to weights exceed or fall below various probability values.

The computer processing systems, computer-implemented methods, apparatus and/or computer program products employ hardware and/or software to solve problems that are highly technical in nature. For example, problems are related to automated processing, determining or inferring differential update rates and/or associated loss function analysis. These problems are not abstract and cannot be performed as a set of mental acts by a human. For example, a human, or even thousands of humans, cannot efficiently, accurately and effectively manually apply countless thousands of node variables to input points and perform analysis to determine that a probability value assigned to a threshold level exceeds a defined probability value.

In order to provide for or aid in the numerous inferences described herein (e.g., inferring data from a medical image), components described herein can examine the entirety or a subset of data to which it is granted access and can provide for reasoning about or inferring states of a system, environment, etc. from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data.

Such inference can result in construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines, etc.) can be employed in connection with performing automatic and/or inferred action in connection with the claimed subject matter.

A classifier can map an input attribute vector, x=(x1, x2, x3, x4, xn), to a confidence that the input belongs to a class, as by f(x)=confidence(class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification with higher accuracy for testing/validation data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

While the disclosed subject matter has been described above in the general context of computer-executable instructions of a computer program product that can be executed on a computer and/or computers, those skilled in the art will recognize that this disclosure also can or can be implemented in combination with other program modules. Generally, program modules can include routines, programs, components, data structures, and the like, that can perform designated tasks and/or implement particular abstract data types. Moreover, those skilled in the art will appreciate that the inventive computer-implemented methods described herein can be practiced with other computer system configurations, including single-processor and/or multiprocessor computer systems, mini-computing devices, mainframe computers, as well as computers, hand-held computing devices (e.g., PDA, cellphone), microprocessor-based and/or programmable consumer and/or industrial electronics, and/or the like. The illustrated aspects described herein can also be practiced in distributed computing environments where tasks are performed by remote processing devices that can be coupled via a communications network, for example. However, some, if not all aspects of this disclosure can be practiced on stand-alone computers. In a distributed computing environment, program modules described herein can be located in both local and/or remote memory storage devices.

As used in this application, the terms "component," "system," "subsystem" "platform," "layer," "gateway," "interface," "service," "application," "device," and the like, can refer to and/or can include one or more computer-related entities and/or an entity related to an operational machine that can have one or more desired functionalities based on the executable instructions described herein. The entities disclosed herein can be implemented via hardware, a combination of hardware and/or software, software, and/or software in execution. For example, a component, as described herein can be, but is not limited to being, a process running on a processor, a processor, an object, an executable, a thread of execution, a program, and/or a computer. By way of illustration, both an application running on a server and the server itself can be a component. One or more components can reside within a process and/or thread of execution and/or a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric and/or electronic circuitry, which is operated by a software and/or firmware application executed by a processor. In such a case, the processor can be internal and/or external to the apparatus executing instructions described herein and can execute at least a part of the software and/or firmware application. As yet another example, a component can be an apparatus that provides desired functionality through electronic components (e.g., without mechanical parts), wherein the electronic components can include a processor and/or other means to execute software and/or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" can be satisfied under any of the foregoing instances. Moreover, articles "a" and "an" as used in the subject specification and annexed drawings should generally be construed to mean "one or more" unless specified otherwise and/or clear from context to be directed to a singular form. As used herein, the terms "example" and/or "exemplary" are utilized to mean serving as an example, instance, and/or illustration and are intended to be non-limiting. For the avoidance of doubt, the subject matter disclosed herein is not limited by such examples. In addition, any aspect and/or design described herein as an "example" and/or "exemplary" is not necessarily to be construed as preferred and/or advantageous over other aspects and/or designs, nor is it meant to preclude equivalent exemplary structures and techniques known to those of ordinary skill in the art.

As it is employed in the subject specification, the term "processor" can refer to substantially any computing processing unit and/or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate and/or transistor logic, discrete hardware components, and/or any combination thereof designed to perform the functions described herein. Further, processors can exploit nano-scale architectures such as, but not limited to, molecular and/or quantum-dot based transistors, switches, gates, and/or gates of switches, in order to optimize space usage and/or enhance performance of entity equipment. A processor can also be implemented as a combination of computing processing units. In this disclosure, terms such as "store," "storage," "data store," data storage," "database," and/or substantially any other information storage component relevant to operation and/or functionality of a component can be utilized to refer to "memory components," entities embodied in a "memory," and/or components comprising a memory. It is to be appreciated that memory and/or memory components described herein can be volatile memory and/or nonvolatile memory, and/or can include both volatile and/or nonvolatile memory. By way of illustration, and not limitation, nonvolatile memory can include read only memory (ROM), programmable ROM (PROM), electrically programmable ROM (EPROM), electrically erasable ROM (EEPROM), flash memory, and/or nonvolatile random-access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM).

Additionally, the disclosed memory components of systems and/or computer-implemented methods described herein are intended to include, without being limited to including, these and/or any other suitable types of memory.

What has been described above includes mere examples of systems and/or computer-implemented methods. It is, of course, not possible to describe every conceivable combination of components and/or computer-implemented methods for purposes of describing this disclosure, but one of ordinary skill in the art can recognize that many further combinations and/or permutations of this disclosure are possible. Furthermore, to the extent that the terms "includes," "has," "possesses," and the like are used in the detailed description, claims, appendices and/or drawings such terms are intended to be inclusive in a manner similar to the term "comprising" as "comprising" is interpreted when employed as a transitional word in a claim. The descriptions of the various examples disclosed herein have been presented for purposes of illustration yet are not intended to be exhaustive and/or limited to the examples disclosed. Many modifications and/or variations can be apparent to those of ordinary skill in the art without departing from the scope and/or spirit of the described examples. The terminology used herein was chosen to best explain the principles of the examples, the practical application and/or technical improvement over technologies found in the marketplace, and/or to enable others of ordinary skill in the art to understand the examples disclosed herein.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further aspects of various embodiments of the subject claimed innovation are provided in the subject matter that follows:

1. A system, comprising: a memory that stores computer-executable components; and a processor, operably coupled to the memory, that executes the computer-executable components stored in the memory, wherein the computer-executable components comprise: a learning network component that determines respective weights assigned to respective node inputs of a learning network in accordance with a learning phase of the learning network and trains a variable separator component to differentially change learning rates of the learning network component; and a differential rate component that applies at least one update learning rate to adjust at least one weight assigned to at least one of the respective node inputs and applies at least one other update learning rate to adjust the respective weight assigned to at least one other of the respective node inputs in accordance with the variable separator component during the learning phase of the learning network.

2. The system of any preceding clause, wherein the learning network is a neural network component that generates output predictions based on received node inputs that are weighted in accordance with the learning phase of the learning network.

3. The system of any preceding clause, further comprising a machine learning application that operates in accordance with the learning network, wherein the machine learning application includes at least one of data classification, data segmentation, data transformation, data detection, data generation, data regression, language generation, machine translation, and sentiment analysis.

4. The system of any preceding clause, wherein training data is provided as the inputs to the neural network component in accordance with the learning phase, the training data is applied to the neural network component for machine learning application processing of a data set, and wherein the training data is employed by the learning component to determine the respective weights associated with the respective node inputs.

5. The system of any preceding clause, wherein the weights describe a relevance of the inputs for the machine learning application processing of the data set, and wherein the update rate applied by the differential rate component provides an adjustment to the respective weights of the respective node inputs in accordance with the variable separator component during the learning phase of the learning network.

6. The system of any preceding clause, wherein the learning component further comprises a loss function component that receives prediction output data from the neural network component in accordance with the learning phase, wherein the prediction output data is generated in response to the respective update rates applied by the differential rate component to adjust the respective weights in accordance with the variable separator component during the learning phase of the learning network.

7. The system of any preceding clause, wherein the loss function component computes an error term (E) associated with a given weight (W), wherein the error term E and the given weight W is associated with an error function ($f$) that describes an amount of error between a predicted output ý of the neural network component versus a desired output y of the neural network component at a selected update learning rate (n) that is applied by the differential rate component in accordance with the variable separator component during the learning phase of the learning network 8. The system of any preceding clause, wherein the differential rate component applies different update learning rates to the node inputs based on the training data according to the following differential rate update equations:

$$\frac{dE}{dW_1}, \frac{dE}{dW_2}, \ldots \ldots = n_1\, f(y, \acute{y}),\, n_2\, f(y, \acute{y}), \ldots \ldots$$

$$\frac{dE_1}{dW_1}, \frac{dE_2}{dW_2}, \ldots \ldots = n_1\, f(y_1, \acute{y}_1),\, n_2\, f(y_2, \acute{y}_2), \ldots \ldots$$

$$\frac{dE_1}{dW_1}, \frac{dE_2}{dW_2}, \ldots \ldots = n_1\, f(y_{a \to b}, \acute{y}_{a \to b}),\, n_2\, f(y_{b \to c}, \acute{y}_{b \to c}), \ldots \ldots$$

Differential Rate Update Equations, wherein E is the error term, $W_1$ are weights assigned to one training data subset, $W_2$ are weights assigned to another training data subset, $n_1$ is the update learning rate for $W_1$ and $n_2$ is the update learning rate for $W_2$, $f$ is the error function ( ), y is the desired output of the neural network component, and is the predicted output of the neural network component.

9. The system of claim 8, further comprising a variable separator component that separates network weights into separate groups for applying different update learning rates generated by the differential rate component.

10. The system of any preceding clause, wherein the different update learning rates applied to the separate network weights enables determination of a correlation based on the error term E and network weights.

11. The system of any preceding clause, wherein differential update learning rates are determined based on the error term E to learn multi-modal data.

12. The system of any preceding clause, further comprising a pattern proposal network that selects different regions of an image, wherein the respective regions selected includes the image or portions of the image based on the selection of types of objects selected in the image.

13. The system of any preceding clause, further comprising a diagnostic learning network that is trained via medical image training data in accordance with the learning phase, wherein the learning component is employed to train the diagnostic learning network to facilitate prediction of a medical condition associated with medical image input data received subsequent to the learning phase.

14. A computer-implemented method, comprising: determining, by a system operatively coupled to a processor, respective weights assigned to respective node inputs of a learning network in accordance with a learning phase of the learning network; applying, by the system, at least one update rate to adjust at least one weight assigned to at least one of the respective node inputs; and applying, by the system, at least one other update rate to adjust the respective weight assigned to at least one other of the respective node inputs in accordance with the learning phase of the learning network.

15. The computer-implemented method of any preceding clause, wherein the learning network is a neural network component that generates output predictions based on received node inputs that are weighted in accordance with the learning phase of the learning network, and wherein training data is provided as the inputs to the neural network component in accordance with the learning phase, the training data is applied to the neural network component for data classification of a data set, and wherein the training data is employed to determine the respective weights associated with the respective node inputs.

16. The computer-implemented method of any preceding clause wherein the weights describe a relevance of the node inputs for the data classification of the data set, and wherein the respective update rate applied provides an adjustment to the respective weights of the respective node inputs in accordance with the learning phase.

17. The computer-implemented method of any preceding clause, further comprising a loss function that computes an error term (E) associated with a given weight (W), wherein the error term E and the given weight W is associated with an error function (f) that describes an amount of error between a predicted output ý of the neural network component versus a desired output y of the neural network component at a selected update rate (n) that is applied in accordance with the learning phase.

18. The computer-implemented method of any preceding clause, further comprising applying different update rates to the respective node inputs based on the training data according to the following differential rate update equations:

$$\frac{dE}{dW_1}, \frac{dE}{dW_2}, \ldots \ldots = n_1 \, f(y, \acute{y}), n_2 \, f(y, \acute{y}), \ldots \ldots$$

$$\frac{dE_1}{dW_1}, \frac{dE_2}{dW_2}, \ldots \ldots = n_1 \, f(y_1, \acute{y}_1), n_2 \, f(y_2, \acute{y}_2), \ldots \ldots$$

$$\frac{dE_1}{dW_1}, \frac{dE_2}{dW_2}, \ldots \ldots = n_1 \, f(y_{a \to b}, \acute{y}_{a \to b}), n_2 \, f(y_{b \to c}, \acute{y}_{b \to c}), \ldots \ldots$$

Differential Rate Update Equations, wherein E is the error term, $W_1$ are weights assigned to one training data subset, $W_2$ are weights assigned to another training data subset, $n_1$ is the update rate for $W_1$ and $n_2$ is the update rate for $W_2$, $f$ is the error function ( ), y is the desired output of the neural network component, and ý is the predicted output of the neural network component.

19. A non-transitory machine-readable storage medium, comprising executable instructions that, when executed by a processor cause the processor to: determine respective weights assigned to respective node inputs of a learning network in accordance with a learning phase of the learning network; apply at least one update rate to adjust at least one weight assigned to at least one of the respective node inputs; and apply at least one other update rate to adjust the respective weight assigned to at least one other of the respective node inputs in accordance with the learning phase of the learning network.

20. The non-transitory machine-readable storage medium of any preceding clause, wherein the learning network is a neural network component that generates output predictions based on received node inputs that are weighted in accordance with the learning phase of the learning network.

What is claimed is:

1. A system, comprising:
a memory that stores computer-executable components; and
a processor, operably coupled to the memory, that executes the computer-executable components stored in the memory, wherein the computer-executable components comprise:
a learning network component that determines respective weights assigned to respective node inputs of a learning network in accordance with a learning phase of the learning network and trains a variable separator component to differentially change learning rates of the learning network component; and
a differential rate component that applies at least one update learning rate to adjust at least one weight assigned to at least one of the respective node inputs and applies at least one other update learning rate to adjust the respective weight assigned to at least one other of the respective node inputs in accordance with the variable separator component during the learning phase of the learning network.

2. The system of claim 1, wherein the learning network is a neural network component that generates output predictions based on received node inputs that are weighted in accordance with the learning phase of the learning network.

3. The system of claim 2, further comprising a machine learning application that operates in accordance with the learning network, wherein the machine learning application includes at least one of data classification, data segmentation, data transformation, data detection, data generation, data regression, language generation, machine translation, and sentiment analysis.

4. The system of claim 3, wherein training data is provided as the inputs to the neural network component in accordance with the learning phase, the training data is applied to the neural network component for machine learning application processing of a data set, and wherein the training data is employed by the learning component to determine the respective weights associated with the respective node inputs.

5. The system of claim 4, wherein the weights describe a relevance of the inputs for the machine learning application processing of the data set, and wherein the update rate applied by the differential rate component provides an adjustment to the respective weights of the respective node inputs in accordance with the variable separator component during the learning phase of the learning network.

6. The system of claim 5, wherein the learning component further comprises a loss function component that receives prediction output data from the neural network component in accordance with the learning phase, wherein the prediction output data is generated in response to the respective update rates applied by the differential rate component to adjust the respective weights in accordance with the variable separator component during the learning phase of the learning network.

7. The system of claim 6, wherein the loss function component computes an error term (E) associated with a given weight (W), wherein the error term E and the given weight W is associated with an error function (f) that describes an amount of error between a predicted output of the neural network component versus a desired output y of the neural network component at a selected update learning rate (n) that is applied by the differential rate component in accordance with the variable separator component during the learning phase of the learning network.

8. The system of claim 7, wherein the differential rate component applies different update learning rates to the node inputs based on the training data according to the following differential rate update equations:

$$\frac{dE}{dW_1}, \frac{dE}{dW_2}, \ldots \ldots = n_1 \, f(y, \acute{y}), n_2 \, f(y, \acute{y}), \ldots \ldots$$

$$\frac{dE_1}{dW_1}, \frac{dE_2}{dW_2}, \ldots \ldots = n_1 \, f(y_1, \acute{y}_1), n_2 \, f(y_2, \acute{y}_2), \ldots \ldots$$

$$\frac{dE_1}{dW_1}, \frac{dE_2}{dW_2}, \ldots \ldots = n_1 \, f(y_{a \to b}, \acute{y}_{a \to b}), n_2 \, f(y_{b \to c}, \acute{y}_{b \to c}), \ldots \ldots$$

wherein E is the error term, $W_1$ are weights assigned to one training data subset, $W_2$ are weights assigned to another training data subset, $n_1$ is the update learning rate for $W_1$ and $n_2$ is the update learning rate for $W_2$, $f$ is the error function ( ), y is the desired output of the neural network component, and ŷ is the predicted output of the neural network component.

9. The system of claim 8, further comprising the variable separator component, and wherein the variable separator component separates network weights into separate groups for applying different update learning rates generated by the differential rate component.

10. The system of claim 9, wherein the different update learning rates applied to the separate network weights enables determination of a correlation based on the error term E and network weights.

11. The system of claim 9, wherein differential update learning rates are determined based on the error term E to learn multi-modal data.

12. The system of claim 9, further comprising a pattern proposal network that selects different regions of an image, wherein the respective regions selected includes the image or portions of the image based on the selection of types of objects selected in the image.

13. The system of claim 1, further comprising a diagnostic learning network that is trained via medical image training data in accordance with the learning phase, wherein the learning component is employed to train the diagnostic learning network to facilitate prediction of a medical condition associated with medical image input data received subsequent to the learning phase.

14. A computer-implemented method, comprising:
  determining, by a learning network component of a system operatively coupled to a processor, respective weights assigned to respective node inputs of a learning network in accordance with a learning phase of the learning network;
  training, by the system, a variable separator component to differentially change learning rates of the learning network component applying, by the system, at least one update learning rate to adjust at least one weight assigned to at least one of the respective node inputs; and
  applying, by the system, at least one other update learning rate to adjust the respective weight assigned to at least one other of the respective node inputs in accordance with the variable separator component during the learning phase of the learning network.

15. The computer-implemented method of claim 14, wherein the learning network is a neural network component that generates output predictions based on received node inputs that are weighted in accordance with the learning phase of the learning network, and wherein training data is provided as the inputs to the neural network component in accordance with the learning phase, the training data is applied to the neural network component for data classification of a data set, and wherein the training data is employed to determine the respective weights associated with the respective node inputs.

16. The computer-implemented method of claim 15, wherein the weights describe a relevance of the node inputs for the data classification of the data set, and wherein the respective update rate applied provides an adjustment to the respective weights of the respective node inputs in accordance with the learning phase.

17. The computer-implemented method of claim 16, further comprising a loss function that computes an error term (E) associated with a given weight (W), wherein the error term E and the given weight W is associated with an error function (ƒ) that describes an amount of error between a predicted output ŷ of the neural network component versus a desired output y of the neural network component at a selected update rate (n) that is applied in accordance with the learning phase.

18. The computer-implemented method of claim 17, further comprising applying different update rates to the respective node inputs based on the training data according to the following differential rate update equations:

$$\frac{dE}{dW_1}, \frac{dE}{dW_2}, \ldots \ldots = n_1 \ f(y, \acute{y}), n_2 \ f(y, \acute{y}), \ldots \ldots$$

$$\frac{dE_1}{dW_1}, \frac{dE_2}{dW_2}, \ldots \ldots = n_1 \ f(y_1, \acute{y}_1), n_2 \ f(y_2, \acute{y}_2), \ldots \ldots$$

$$\frac{dE_1}{dW_1}, \frac{dE_2}{dW_2}, \ldots \ldots = n_1 \ f(y_{a \to b}, \acute{y}_{a \to b}), n_2 \ f(y_{b \to c}, \acute{y}_{b \to c}), \ldots \ldots$$

wherein E is the error term, $W_1$ are weights assigned to one training data subset, $W_2$ are weights assigned to another training data subset, $n_1$ is the update rate for $W_1$ and $n_2$ is the update rate for $W_2$, ƒ is the error function ( ), y is the desired output of the neural network component, and ŷ is the predicted output of the neural network component.

19. A non-transitory machine-readable storage medium, comprising executable instructions that, when executed by a processor cause the processor to:
  determine, by a learning network component, respective weights assigned to respective node inputs of a learning network in accordance with a learning phase of the learning network;
  train a variable separator component to differentially change learning rates of the learning network component;
  apply at least one update learning rate to adjust at least one weight assigned to at least one of the respective node inputs; and
  apply at least one other update learning rate to adjust the respective weight assigned to at least one other of the respective node inputs in accordance with the variable separator component during the learning phase of the learning network.

20. The non-transitory machine-readable storage medium of claim 19, wherein the learning network is a neural network component that generates output predictions based on received node inputs that are weighted in accordance with the learning phase of the learning network.

* * * * *